(12) United States Patent
Bronner et al.

(10) Patent No.: US 7,199,218 B1
(45) Date of Patent: Apr. 3, 2007

(54) ICBP90 POLYPEPTIDE AND ITS FRAGMENTS AND POLYNUCLEOTIDES CODING FOR SAID POLYPEPTIDES AND APPLICATIONS FOR DIAGNOSING AND TREATING CANCER

(75) Inventors: Christian Bronner, Fegersheim (FR); Raphaël Hopfner, Strasbourg (FR); Marc Mousli, Illkirch (FR); Jean-Marc Jeltsch, Molsheim (FR); Yves Lutz, Strasbourg (FR); Pierre Oudet, Strasbourg (FR)

(73) Assignee: Institut National de la Sante et de la Recherche Medicale :(INSERM), Paris (FR)

( * ) Notice: Subject to any disclaimer, the term of this patent is extended or adjusted under 35 U.S.C. 154(b) by 410 days.

(21) Appl. No.: 10/019,071

(22) PCT Filed: Jun. 22, 2000

(86) PCT No.: PCT/FR00/01747

§ 371 (c)(1),
(2), (4) Date: May 15, 2002

(87) PCT Pub. No.: WO00/78949

PCT Pub. Date: Dec. 28, 2000

(30) Foreign Application Priority Data

Jun. 22, 1999 (FR) .................................. 99 07935

(51) Int. Cl.
*C07K 14/00* (2006.01)
(52) U.S. Cl. ................ 530/350; 424/184.1; 424/185.1; 530/827; 530/828
(58) Field of Classification Search ................ 530/350, 530/358, 827, 828; 424/130.1, 184.1, 185.1; 514/2
See application file for complete search history.

(56) References Cited

U.S. PATENT DOCUMENTS 6,551,795 B1 *  4/2003  Rubenfield et al. ......... 435/69.1
6,583,275 B1 *  6/2003  Doucette-Stamm et al. ..... 536/23.1

FOREIGN PATENT DOCUMENTS

WO    WO 98 37207 A    8/1998
WO    WO 99 38971 A    8/1999

OTHER PUBLICATIONS

Bowie et al (Science, 1990, 257 : 1306-1310).*
Drexler et al (Leukemia and Lymphoma, 1993, 9:1-25).*
Embleton et al (Immunol Ser, 1984, 23:181-207).*
Hsu (in Tissue Culture Methods and Applications, Kruse and Patterson, Eds, 1973, Academic Press, NY, see abstract, p. 764).*
Gura (Science, 1997, 278:1041-1042).*
Jain (Sci. Am., 1994, 271:58-65).*
Curti (Crit. Rev. in Oncology/Hematology, 1993, 14:29-39.*
Hartwell et al (Science, 1997, 278:1064-1068).*
Ezzell (J. NIH Res, 1995, 7:46-49.*
Spitler (Cancer Biotherapy, 1995, 10:1-3).*
Boon (Adv Can Res, 1992, 58:177-210).*
Burgess et al, (Journal of Cell Biology, 1990, 11: 2129-2138).*
Lazar et al. Molecular and Cell Biology, 1988, 8: 1247-1252.*
MPSRCH search report, 2004, us-10-019-071-2.olig.rai, pp. 1-2.*
Ronchi, A et al, 1995, Nucleic acids Res, 23(22): 4565-72.*
Liberati, C et al, 1999, J Mol Biol, 285(4) : 1441-55.*
Sugiura et al, 2003, FEBS letters, 537(1-3): 58-62.*
Hopfner, R et al, Jan. 1, 2000, Cancer Res, 60(1): 121-128.*
MPSRCH search report, 2004, us-10-019-071-2.rup, pp. 1-2.*
Austin, C. A., et al., "Novel HeLa topoisomerase II is the IIβ isoform: complete coding sequence and homology with other type II topoisomerases", Biochimica et Biophysica Acta, vol. 1172, pp. 283-291 (1993).
Banerji, J., et al., "Expression of a β-Globin Gene Is Enhanced by Remote SV40 DNA Sequences", Cell, vol. 27, pp. 299-308 (Part 1) (1981).
Barany, F., "Genetic disease detection and DNA amplification using cloned thermostable ligase", Proc. Natl. Acad. Sci., vol. 88, pp. 189-193 (1991).
Boritzki, T. J., "Inhibition of Type II Topoisomerase By Fostriecin", Biochemical Pharmacology, vol. 37, No. 21, pp. 4063-4068 (1988).
Brady, M. E., et al., "Tip60 Is a Nuclear Hormone Receptor Coactivator", J. Biol. Chem., vol. 274, No. 25, pp. 17599-17604 (1999).
Brandt, T. L., et al., "c-Myb *trans*-Activates the Human DNA Topoisomerase IIα Gene Promoter", j. Biol. Chem., vol. 272, No. 10, pp. 6278-6284 (1997).
Brou, C., et al., "Distinct TFIID complexes mediate the effect of different transcriptional activators", EMBO Journal, vol. 12, No. 2, pp. 489-499 (1993).

(Continued)

*Primary Examiner*—Susan Ungar
*Assistant Examiner*—Minh-Tam Davis
(74) *Attorney, Agent, or Firm*—Foley & Lardner LLP

(57) ABSTRACT

The invention concerns a novel ICBP90 (Inverted CCAAT box binding protein 90) and its fragments, polynucleotides coding for said polypeptides and specific antibodies directed against said polypeptides. The invention also concerns methods and kits for diagnosing cell proliferation and compounds useful as medicine for preventing and/or treating pathology involving cell proliferation and in particular cancer.

2 Claims, 11 Drawing Sheets

OTHER PUBLICATIONS

Buckholz, R. G., "Yeast systems for the expression of heterologous gene products", Current Opinion in Biotechnology, vol. 4, pp. 538-542 (1993).

Burg, J. L., et al., "Single molecule detection of RNA reporter probes by amplification with Qβ replicase", Molecular and Cellular Probes, vol. 10, pp. 257-271 (1996).

Chu, B. C. F., et al., "Synthesis of an amplifiable reporter RNA for bioassays", Nucleic Acids Research, vol. 14, No. 14, pp. 5591-5603 (1986).

Chung, T. D. Y., et al., "Characterization and immunological identification of cDNA clones encoding two human DNA topoisomerase II isozymes", Proc. Natl. Acad. Sci., vol. 86, pp. 9431-9435 (1989).

Darzynkiewicz, Z., et al., "Analysis of DNA Content and Cyclin Protein Expression in Studies of DNA Ploidy, Growth Fraction, Lymphocyte Stimulation, and the Cell Cycle", Methods IN Cell Biolgoy, vol. 41, pp. 421-435 (1994).

Deffie, A. M., et al., "Direct Correlation between DNA Topoisomerase II Activity and Cytotoxicity in Adriamycin-sensitive and -resistant P388 Leukemia Cell Lines", Cancer Research, vol. 49, No. 1, pp. 58-62 (1989).

De Vries, L., et al., "GAIP, a protein that specifically interacts with the trimeric G Protein $G\alpha_{i3}$, is a member of a protein family with a highly conserved core domain", Proc. Natl. Acad. Sci., vol. 92, pp. 11916-11920 (1995).

Devys, D., et al., "The FMR-1 protein is cytoplasmic most abundant in neurons and appears normal in carriers of a fragile X premutation", Nature Genetics, vol. 4, pp. 335-340 (1993).

Drake, F. H., et al., "Biochemical and Pharmacological Properties of p170 and p180 Forms of Topoisomerase II", Biochemistry, vol. 28, pp. 8154-8160 (1989).

Duck, P., et al., "Probe Amplifier System Based on Chimeric Cycling Oligonucleotides", BioTechniques, vol. 9, No. 2, pp. 142-147 (1990).

Edwards, C. P., et al., "Current applications of COS cell based transient expression systems", Current Opinion in Biotechnology, vol. 4, pp. 558-563 (1993).

Flouriot, G., et al., "Differentially Expressed Messenger RNA Isoforms of the Human Estrogen Receptor-α Gene Are Generated by Alternative Splicing and Promoter Usage", Mol. Endo., vol. 12, No. 12, pp. 1939-1954 (1998).

Fry, A. M., et al., "Relationship between Topoisomerase II Level and Chemosensitivty in Human Tumor Cell Lines", Cancer Research, vol. 51, pp. 6592-6595 (1991).

Furth, P. A., et al., "Gene Transfer into Somatic Tissues by Jet Injection", Analytical Biochemistry, vol. 205, pp. 365-368 (1992).

Gaub, M-P., et al., "Nuclear Detection of Cellular Retinoic Acid Binding Proteins I and II with New Antibodies", J. Histochem. & Cytochem., vol. 46, No. 10, pp. 1103-1111 (1998).

Goetz, J., et al., "Structure and Expression of the ATFα Gene", J. Biol. Chem., vol. 271, No. 47, pp. 29589-29598 (1996).

Goswami, P. C., et al., "The Cell Cycle-Coupled Expression of Topoisomerase IIα during S Phase Is Regulated by mRNA Stability and Is Disrupted by Heat Shock or Ionizing Radiation", Mole. And Cell. Biol., vol. 16, No. 4, pp. 1500-1508 (1996).

Grandien, K., "Determination of transcription start sites in the human estrogen receptor gene and identification of novel, tissue-specific, estrogen receptor-mRNA isoform", Mole. & Cell. Endoc., vol. 116, pp. 207-212 (1996).

Griffin, C., et al., "Two Functionally Different Protein Isoforms Are Produced from the Chicken Estrogen Receptor-α Gene", Mol. Endo., vol. 13, No. 9, pp. 1571-1587 (1999).

Gruber, S. B., et al., "Pathogenesis of Adenocarcinoma in Peutz-Jeghers Syndrome", Cancer Research, vol. 58, pp. 5267-5270 (1998).

Guatelli, J. C., et al., "Isothermal, in vitro amplification of nucleic acids by a multienzyme reaction modeled after retroviral replication", Proc. Natl. Acad. Sci., vol. 87, pp. 1874-1878 (1990).

Guinee, Jr., D. G., et al., "Comparison of DNA Topoisomerase IIα Expression in Small Cell and Nonsmall Cell Carcinoma of the Lung", Cancer, vol. 78, No. 4, pp. 729-735 (1996).

Haddad, B. R., et al., "Identification of de novo chromosomal markers and derivatives by spectral karyotyping", Hum Genet, vol. 103, pp. 619-625 (1998).

Heck, M. M. S., "Differential expression of DNA topoisomerases I and II during the eukaryotic cell cycle", Proc. Natl. Acad. Sci., vol. 85, pp. 1086-1090 (1988).

Hochhauser, D., et al., "Cloning and Characterization of the 5'-Flanking Region of the Human Topoisomerase IIα Gene", J. Biol. Chem., vol. 267, No. 26, pp. 18961-18965 (1992).

Höglund, M., et al., "Cytogenetic and Fluorescence In Situ Hybridization Analyses of Chromosome 19 Aberrations in Pancrastic Carcinomas: Frequent Loss of 19p13.3 and Gain of 19q13.1-13.2", Genes, Chromosomes & Cancer, vol. 21, pp. 8-16 (1998).

Hromas, R., et al., "Hematopoietic Transcriptional Regulation by the Myeloid Zinc Finger Gene, MZF-1", Molecular Aspects of Myeloid Stem Cell Development, pp. 159-164, Springer-Verlag (1996).

Inouye, C., et al., "Isolation of a cDNA Encoding a Metal Response Element Binding Protein Using a Novel Expression Cloning Procedure: The One Hybrid System", DNA and Cell Biology, vol. 13, No. 7, pp. 731-742 (1994).

Isaacs, R. J., et al., "Physiological regulation of eukaryotic topoisomerase II", Biochimica et Biophysica Acta, vol. 1400, pp. 121-137 (1998).

Jenkins, J. R., et al., "Isolation of cDNA clones encoding the β isozyme of human DNA topoisomerase II and localization of the gene to chromosome 3p24", Nucleic Acids Research, vol. 20, No. 21, pp. 5587-5592 (1992).

Kassel, O., et al., "Up- and Down-Regulation by Glucocorticoids of the Constitutive Expression of the Mast Cell Growth Factor Stem Cell Factor by Human Lung Fibroblasts in Culture", Mol. Pharm., vol. 54, pp. 1073-1079 (1998).

Kennerdell, J. R., et al., "Use of dsRNA-Mediated Genetic Interference to Demonstrate that *frizzled* and *frizzled* 2 Act in the Wingless Pathway", Cell, vol. 95, pp. 1017-1026 (1998).

Kessler, C., et al., Nonradioactive Labeling and Detection of Biomolecules: Overview of Amplification Systems, pp. 197-205, Springer-Verlag, Berlin (1992).

Kievits, T., et al., "NASBA™ isothermal enzymatic in vitro nucleic acid amplification optimized for the diagnosis of HIV-1 infection", J. Virol. Meth., vol. 35, No. 3, pp. 273-286 (1991).

Köhler, G., et al., "Continuous cultures of fused cells secreting antibody of predefined specificity", Nature, vol. 256, No. 5517, pp. 495-497 (1975).

Kwoh, D. Y., et al., "Transcription-based amplification system and detection of amplified human immunodeficiency virus type 1 with a bead-based sandwich hybridization format", Proc. Natl. Acad. Sci., vol. 86, pp. 1173-1177 (1989).

Landegren, U., et al., "A Ligase-Mediated Gene Detection Technique", Science, vol. 241, pp. 1077-1080 (1988).

Lavie, J., et al., "Vascular Cell Adhesion Molecule-1 Gene Expression during Human Smooth Muscle Cell Differentiation Is Independent of NF-κB Activation", J. Biol. Chem., vol. 274, No. 4, pp. 2308-2314 (1999).

Lee, J. Y., et al., "A Distinct Region of Chromosome 19p13.3 Associated with the Sporadic Form of Adenoma Malignum of the Uterine Cervix", Cancer Research, vol. 58, pp. 1140-1143 (1998).

Lizardi, P. M., et al., "Exponential Amplification of Recombinant-RNA Hybridization Probes", Biotech., vol. 6, pp. 1197-1202 (1998).

Luckow, V. A., "Baculovirus systems for the expression of human gene products", Current Opinion in Biotechnology, vol. 4, pp. 564-572 (1993).

Martinez, R., et al., "Gene Structure, Promoter Activity, and Chromosomal Location of the DR-nm23 Gene, a Related Member of the nm23 Gene Family", Cancer Research, vol. 57, pp. 1180-1187 (1997).

Matthews, J. A., et al., "Analytical Strategies for the Use of DNA Probes", Anal. Biochem., vol. 169, pp. 1-25 (1988).

Miele, E. A., "Autocatalytic Replication of a Recombinant RNA", J. Mol. Biol., vol. 171, pp. 281-295 (1983).

Nagase, T., et al., "Promoter Region of the Human CRE-BP1 Gene Encoding the Transcriptional Regulator Binding to the Cyclic AMP Response Element", J. Biol. Chem., vol. 265, No. 28, pp. 17300-17306 (1990).

Nitiss, J. L., "Investigating the biological functions of DNA topoisomerases in eukaryotic cells", Biochimica et Bioplysica Acta, vol. 1400, pp. 63-81 (1998).

Olins, P. O., et al., "Recent advances in heterologous gene expression in *Escherichia coli*", Current Opinion in Biotechnology, vol. 4, pp. 520-525 (1993).

PCR Protocols: *A Guide To Methods and Applications*, Innis, M. A., et al., Academic Press, Inc. (1990), pages ? Reviewed but cannot be published.

PCR Technology, "Principles and Applications for DNA Amplification", Erlich, H. A., Stockton Press, year, page ? Reviewed but cannot be published.

*PCR Topics*, Rolfs, A., et al., Springer-Verlag, Berlin (1990), page? Reviewed but cannot be published.

Pommier, Y., et al., "Cellular Determinants of Sensitivity and Resistance to DNA Topoisomerase Inhibitors", Cancer Investigation, vol. 12, No. 5, pp. 530-542 (1994).

Ponglikitmongkol, M., et al., "Genomic organization of the human oestrogen receptor gene", EMBO Journal, vol. 7, No. 11, pp. 3385-3388 (1988).

Rio, M. C., et al., Specific expression of the pS2 gene in subclasses of breast cancers in comparison with expression of the estrogen and progesterone receptors and the oncogene *ERBB2*, Proc. Natl. Acad. Sci., vol. 84, pp. 9243-9247 (1987).

Qian, F., et al., "Chromosomal Localization of the Four Genes (NFIA, B, C, and X) for the Human Transcription Factor Nuclear Factor I by FISH", Genomics, vol. 28, pp. 66-73 (1995).

Rochette-Egly, C., et al., "Stimulation of RARα Activation Function AF-1 through Binding to the General Transcription Factor TFIIH and Phosphorylation by CDK7", Cell, vol. 90, pp. 97-107 (1997).

Roskell, D. E., et al., "Proliferating Cell Nuclear Antigen Expression Grossly Over-estimates Cellular Proliferation in Cardiac Myxomas", Eur. J. Med. Res., vol. 4, pp. 105-106 (1999).

Sambrook, J., et al., Molecular Cloning: A Laboratory Manual, 2d ed., Cold spring Harbor Laboratory Press (1989).

Sherer, M. E., et al., "Atypical (7;19) Translocation in Actue Myelomonocytic Leukemia", Cancer Genet Cytogenet, vol. 57, pp. 169-173 (1991).

Stone, B. B., et al., "Detection of rRNA from four respiratory pathogens using an automated Qβ replicase assay", Molecular and Cellular Probes, vol. 10, pp. 359-370 (1996).

Tang, D., et al., "Genetic immunization is a simple method for elicitng an immune response", Nature, vol. 356, No. 6365, pp. 152-154 (1992).

Taniwaki, M., et al., "Non-Random Chromosomal Rearrangements and Their Implications in Clinical Features and Outcome of Multiple Myeloma and Plasma Cell Leukemia", Leukemia and Lymphoma, vol. 21, pp. 25-30 (1995).

Tsai-Pflugfelder, M., et al., "Cloning and sequencing of cDNA encoding human DNA topoisomerase II and localization of the gene to chromosome region 17q21-22", Proc. Natl. Acad. Sci., vol. 85, pp. 7177-7181 (1988).

Walker, G. T., et al., "Strand displacement amplification—an isothermal, *in vitro* DNA amplification technique", Nucleic Acids Research, vol. 20, No. 7, pp. 1691-1696 (1992).

Wang, J. C., "DNA Topoisomerases", Annu. Rev. Biochem., vol. 65, pp. 635-692 (1996).

Wang, M. M., et al., "Molecular cloning of the olfactory neuronal transcription factor Olf-1 by genetic selection in yeast", Nature, vol. 364, No. 6433, pp. 121-126 (1993).

Yamazaki, K., et al., "Quantitative immunocytochemical assays of toposisomerase II in Lung Adenocarcinoma Cell Lines", Acta Oncologica, vol. 35, No. 4, pp. 417-423 (1996).

Database EMBL Nucleotide and Protein Sequences, "Homo sapiens cDNA clone Image: 1750886 3' similar to TR:015871 015871 Ubiquitin, rRNA sequence", XP002133353 (Aug. 18, 1998).

Database EMBL Nucleotide and Protein Sequences, "Homo sapiens cDNA 5'", clone Image: 1750886 3' similar to TR:015871 015871 Ubiquitin, Rrna sequence, XP002133354 (Apr. 18, 1997).

Database EMBL Nucleotide and Protein Sequences, Homo sapiens chromosome 19 clone CTC-518P12, Working Draft Sequence, 84 unordered pieces, XP002148667 (Apr. 3, 2000).

Fujimori, A., et al., "Cloning and mapping of Np96 gene which encodes a novel nuclear protein associated with cell proliferation", Mammalian Genome, vol. 9, No. 12, pp. 1032-1035 (1998) (XP000890078).

Herzog, C. E., et al., "Evaluation of a potential regulatory role for inverted CCAAT boxes in the human topoisomerase IIalpha promoter", Biochemical and Biophysical Research Communications, vol. 232, pp. 608-612 (1997) (XP000877157).

Hopfner, R., et al., "ICBP90, a novel human CCAAT binding protein, involved in the regulation of topoisomerase IIalpha expression", Cancer Research, vol. 60, No. 1, pp. 121-128 (Jan. 1, 2000) (XP0008884566).

Isaacs, R. J., et al., "Regulation of the human topoisomeraase IIalpha gene promoter in confluence arrested cells", The Journal of Biological Chemistry, vol. 271, No. 28, pp. 16741-16747 (Jul. 12, 1996) (XP002133355).

Kubo, T., et al,. "DNA topoisomerase IIalpha gene expression under transcriptional control in etoposide/teniposide-resistant human cancer cells", Cancer Research, vol. 55, pp. 3860-3864 (Sep. 1, 1995) (XP000877419).

Lim, K., et al., "Reduced level of ATF is correlated with transcriptional repression of DNA topoisomerase IIalpha gene during TPA-induced differentiation HL-60 cells", Biochemistry and Molecular Biology Intl., vol. 46, No. 1, pp. 35-42 (Sep. 1, 1998) (XP000900088).

Sandri, M. I., et al., P53 Regulates the minimal promoter of the human nucleic acids research, GB, Oxford University Press, Surrey, vol. 24, No. 22, pp. 4464-4470 (Nov. 15, 1996) (XP002068824).

* cited by examiner

```
   1 ATGTGGATCC AGGTTCGGAC CATGGATGGG AGGCAGAGACCC ACACGGTGGA CTCGCTGTCC AGGCTGACCA AGTGGAGGA   80
  81 GCTGAGGCGG AAGATCCAGG AGCTGTTCCA CGTGGAGCGA            GGCCTGCAGA GGCTGTTCTA CAGGGCAAA CAGATGGAGG  160
 161 ACGGCCATAC CCTCTTCGAC TACGAGGTCC GCCTGAATGA            CACCATCCAG CTCCTGGTCC GCCAGAGCCT CGTGCTCCCC  240
 241 CACAGCACCA AGGAGGGGA CTCCGAGCTC TCCGACACCG            ACTCCGGTGG CTGCCTGGGC GAGAGTGAGT CAGACAAGTC  320
 321 CTCCACCCAC GGTGAGGCGG CCGCCGAGAC TGACAGCAGG            CCAGCCGATG AGGACATGTG GGATGAGACG GAATTGGGGC  400
 401 TGTACAAGT  CAATGAGTAC GTCGATGCTC GGGACACGAA            CATGGGGCGG TGGTTTGAGG CGCAGGTGGT CAGGGTGACG  480
 481 CGGAAGGCCC CCTCCGGGA CGAGCCCTGC AGTCCACGT            CCAGGCCGC GCTGGAGGAG GACGTCATTT ACCACGTGAA  560
 561 ATACGACGAC TACCCGGAGA ACGGCGTGGT CCAGATGAAC            TCCAGGGACG TCCGAGCGCG CCCCCGCACC ATCATCAAGT  640
 641 GGCAGGACCT GGAGGTGGGC CAGGTGGTCA TGCTCAACTA            CAACCCCAAGG AGCCGGGCTT CTGGTACGAC  720
 721 GCGGAGATCT CCAGGAAGCG CGAGACCAGC ACGGCGCGG            AACTCAGCC CAACGTGGTG CCCCATGGAG ATTCTCTGAA  800
 801 CGACTGTCGG ATCATCTTCG TGGACGAAGT CTTCAAGATT            GAGCGGGCCG GTGAAGGAG CCCCATGGTT GACAACCCA  880
 881 TGAGACGGAA GAGCGGGCCG TCCTGCAAGC ACTGCAAGGA            CGACGTGAAC AGACTCTGCA GGGTCTGCGC CTGCCACCTG  960
 961 TGCGGGGGCC GGCAGGACCC CGACAAGCAG CTCATGTGCG            ATGAGTGCGA CATGGCCTTC GCCTGACCT GTACTGGCGG 1040
1041 GCCCCTCAGC AGTGTTCCA GCGAGGACGA GTGGTACTGC            CCTGAGTGCC GGAATGATGC CAGCGAGGTG GGGCAAGGGC 1120
1121 GAGAGCGGCT GAGAGAGAGC AAGAAGAATG CGAAGATGGC            CTCGGCCACA TGTCCTCAC AGCGGACTG ATCCCGTGGG 1200
1201 ATGGCCTGTG TGGGCCGCAC CAAGGAATGT ACCATCGTCC            CGTCCAACCA CTACGACCC ATCCCGGGA TGGCCGGAGCA 1280
1281 CACCATGTGG CGGTTCCGAG TCCAGGTCAG CGAGTCGAG            GTCCATCGC CCCACGTGG TGGCATCCAT GGCCGGAGCA 1360
1361 ACGACGGATC GTACTCCCTA GTCCTGGCGG GGGCTATGA            GGATGATGTG GACCATGGGA ATTTTTTCAC ATACACGGGT 1440
1441 AGTGGTGGTC GAGATCTTTC CGGCAACAAG AGGACCGCGG            AACAGTCTTG TGATCAGAAA CTCACCAACA CCAACAGGGC 1520
1521 GCTGCTCTC AACTGCTTTG CTCCCATGAA TGACCAAGAA            CCAAGGCCGA GG CCAAGGACTG GCGGTCGGG AAGCCGGTCA 1600
1601 GGTGGTGCG CAATGTCAAG GGTGGCAAGA ATAGCAAGTA            CGCCCCGCT GAGGGCAACC GCTACGATGG CATCTACAAG 1680
1681 GTTGTGAAT ACTGGGCCGA GAAGGGGAAG GAAGGGTTTC            TGTGTGCG CTACCTTCTG CGGAGGACG ATGATGAGCC 1760
1761 TGGCCCTTGG ACGAAGGAGG GGAAGGACCG GATCAAGAAG            CTGGGGCTGA CCATGCAGTA TCCAGAAGGC TACCTGGAAG 1840
1841 CCCTGGCCAA CCGAGAGCGA GAGAAGGAGA ACAGCAAGAG            GGAGGCCCGA GAGCAGCAGG AGGGGGGCTT CGGCTCCCCC 1920
1921 AGGACGGGCA GAAGCAAGTG GAAGCGGAAG TCGGCAGGAG            GTGGCCCGAG CAGGGCCGGG TCCCCGCGCC CGACATCCAA 2000
2001 GAAAACCAAG GTGGAGCCCT ACAGTCTCAC GGCCCAGCAG            AGCAGCCTCA TCAGAGAGGA CAAGGACAAC GCCAAGCTGT 2080
2081 GGAATGAGT CTGGCGTCA CTCAAGGACG GGCCGGCAG            CGGCAGCCG TTCCAGTTGT TCTGAGTAA GTGGAGGAG GCAAGGACTG 2160
2161 ACGTTCCAGT GTATCTGCTG TCAGGAGCTG GTGTTCCGGC            CCATCACGAC CGTGTGCCAG CACAACGTGT GCAAGGACTG 2240
2241 CCTGGACAGA TCCTTTCGGG CACAGGTGTT CAGCTGCCCT            GCCGCGCT ACAGCTGGGG CCGAGCTGGG CCAGCTGGGG CCATGCAGG 2320
2321 TGAACCAGCC TCTGCAGACC GTCCTCAACC AGTCTCTCCC            GGCTACGGC AATGGCGGGT GA                       2382
       —         —         —         —         —         —         —         —
       10        20        30        40        50        60        70        80
```

FIG_6

```
  1 MWIQVRTMDG RQTHTVDSLS RLTKVEELRR KIQELFHVEP GLQRLFYRGK QHEDGHTLFD YEVRLNDTIQ LLVRQSLVLP  80
 81 HSTKERDSEL SDTDSGCCLG QSESDKSSTH GEAAAETDSR PADEDMWDET ELGLYKVNEY VDARDTNMGA WFEAQVVRVT 160
161 RKAPSRDEPC SSTSRPALEE DVIYHVKYDD YPENGVVQMN SRDVRARART IIKWQDLEVG QVVHLNYNPD NPKERGFWYD 240
241 AEISRKRETR TARELYANVV LGDDSLNDCR IIFVDEVFKI ERPGEGSPMV DNPMRRKSGP SCKHCKDDVN RLCRVCACHL 320
321 CGGRQDPDKQ LMCDECDMAF HIYCLDPPLS SVPSEDEMYC PECRNDASEV VLAGERLRES KKNAKMASAI SSSQRDWGKG 400
401 MACVGRTKEC TIVPSNHYGP IPGIPVGTMW RFRVQVSESG VHRPHVAGIH GRSNDGSYSL VLAGGYEDDV DHGNFFTYTG 480
481 SGGRDLSGNK RTAEQSCDQK LINTNRALAL NCFAPINDQE GAEAKDWRSG KPVRVRNVK GGKNSKYAPA EGNRYDGIYK 560
561 VVKYWPEKGK SGFLVMRYLL RDDDEPGPW TKEGKDRIKK LQLTMQYPEG YLEALANRER EKENSKREEE EQQEGGFASP 640
641 RIGKGKWKRK SAGGGPSRAG SPRRTSKKTK VEPYSLIAQQ SSLIREDKSN AKLWNEVLAS LKDRPASGSP FQLFLSKVEE 720
721 TFQCICCQEL VFRPITTVCQ KNVCKDCLDR SFRAQVFSCP ACRYDLGRSY AMQVNQPLQT VLNQLFPGIG NGR*        794
        |          |          |          |          |          |          |          |
       10         20         30         40         50         60         70         80
```

FIG_7

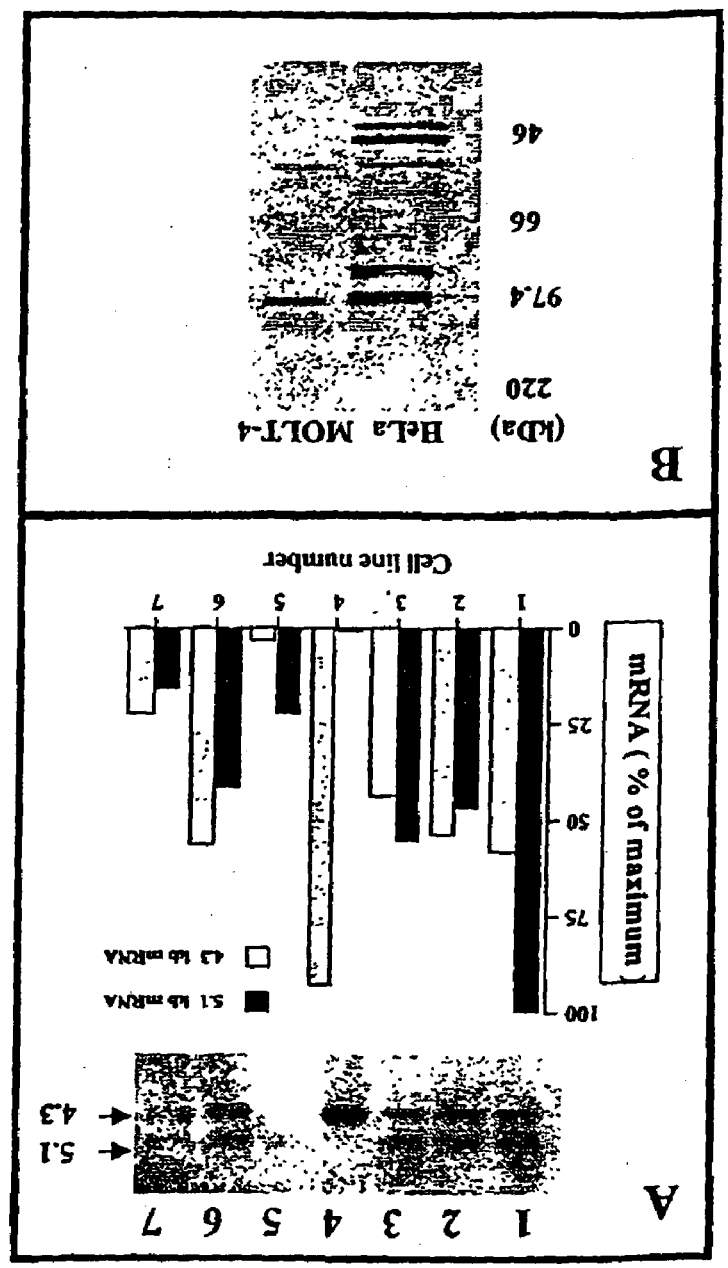

ICBP90 POLYPEPTIDE AND ITS FRAGMENTS AND POLYNUCLEOTIDES CODING FOR SAID POLYPEPTIDES AND APPLICATIONS FOR DIAGNOSING AND TREATING CANCER

This application is a national stage entry under 35 U.S.C. § 371 of PCT patent application no. 99/07935 filed on Jun. 22, 2000, which claims priority to French patent application no. FR99/07935, filed on Jun. 22, 1999.

The present invention relates to a new ICBP90 polypeptide and its fragments, to the cloning of cDNA and polynucleotides coding for said polypeptides, to cloning and/or expression vectors including said polynucleotides, cells transformed by said vectors and specific antibodies directed against said polypeptides. The invention also relates to methods and kits for diagnosing cancers, to a method and kit for screening ligands of the polypeptides of the invention and of compounds which may be used as a drug for prevention and/or treatment of cancers.

DNA topoisomerases are highly preserved nuclear proteins during evolution, the main role of which is for controlling DNA conformation and topology in the nucleus, which are constantly altered by the various biological processes involving DNA such as for example, transcription and replication. Topoisomerases exert their action by cutting DNA and linking these lesions after having achieved the adequate conformational change.

In mammals and humans in particular, today, there are at least five different genes coding for a topoisomerase and at least two additional pseudogenes (for a review, see Nitiss 1998). Thus, topoisomerase I, coded by the TOP1 gene removes the superturns present in DNA while only cutting a single strand. Both topoisomerases of type II existing in humans called TopIIα and TopIIβ, alter DNA topology by introducing transient double strand cleavages (for a review, see Wang 1996). Finally, there are two topoisomerases of type III coded by two localized genes in 17p11.2-12 and 22q11-12 and they only act against negative superturns of DNA.

In tumoral cells, topoisomerases of type II play a very important role; in these growing and rapidly dividing cells, there is a large need for maintaining DNA molecules in a proper conformation as high transcription and replication rates are required. Thus, the rates for topoisomerase II are generally higher in human tumoral cells than in normal tissues of the same origin. However, the high expression rate of topoisomerase IIα in tumoral cells may vary among two tumors of different natures affecting a same tissue. For example, the nucleus of cells from small cell carcinomas of the lung has a higher rate of topoisomerase IIα than the nucleus of cells from lung carcinomas with normal sized cells (Guinee et al., 1996). In the same way, the rate of topoisomerase IIα in A59 cells is three times higher than in PC3 cells, both of these cell lines stemming from the adenocarcinoma of lung epithelium (Yamasaki et al., 1996).

These observations suggest that topoisomerase IIα may be considered as a marker of cell proliferation for certain types of cancer. As the cancerous process is characterized by abnormal cell proliferation partly due to the loss of contact inhibition, topoisomerase IIα therefore appears as a preferential target for chemotherapeutical drugs for treating cancer (Pommier et al., 1994), and the present anticancer treatments largely resort to inhibitors of topoisomerases.

Most of these inhibitors exert their cytotoxic effects by stabilizing the DNA cleavage complex. Drugs like anthracyclines [doxorubicin (adriamycin) or epipodophyllotoxins (such as etoposide (VP-16) or teniposide (VM26))], acridines (such as mAMSA) and anthracendiones (for example, mitoxantrone) are examples of drugs which inhibit topoisomerases II which stabilize the cleavage complex. More recently, a new class of inhibitors of topoisomerases II has been developed; these inhibitors act at the level of catalytic activity and no longer by stabilizing the cleavage complex. The drug, fostriecin is an example of one of them (Boritzki et al., 1988). Today these different drugs are used in palliative and curative anticancer treatments.

Nevertheless, one of the major problems encountered in the present anticancer treatments using inhibitors of topoisomerases is the emergence of a resistance to drugs (Kubo et al., 1995). These resistances are either the occurrence of an overexpression of pumps providing efflux of drugs outside the cells before they reach their target (for example; P-glycoprotein, a protein associated with multi-drug resistance (MRP)), or the occurrence of a change in the expression rate of topoisomerase IIα (Deffie et al., 1989; Fry et al., 1991), or either both occurrences (for a review, see Isaacs et al., 1998).

One of the aspects of the present invention is therefore to understand the regulatory mechanisms of the expression of the gene of topoisomerase IIα, in order to develop an alternative to the phenomenon of resistance to drugs, observed for certain cancers and this with the aim of enhancing the curative and preventive treatment of cancers.

There are two types of type II topoisomerase which differ in their expression profile; topoisomerase IIα (Top IIα) (170 kD), essentially located in the nucleoplasm at the centromer of the mitotic chromosomes, participates in the fundamental biological processes which are replication, condensation of chromosomes and transcription. It seems that topoisomerase IIβ (Top II (180 kD) is rather involved in the transcription of ribosomal RNA, given the nucleolar localization of this enzyme. Both human type II topoisomerases are localized on two different chromosomes (17q21-22 for topoisomerase IIα and 3p24 for topoisomerase IIβ) (Tsai-Plugfelder et al, 1988; Drake et al., 1989; Chung et al., 1989; Jenkins et al., 1992; Austin et al., 1993).

Unlike topoisomerase IIβ, the expression of which is characterized by a relative consistency, topoisomerase IIα has a variation of expression depending on the proliferation state of cells and on their position in the cell cycle. Expression of messenger RNA (RNAm) is higher in proliferating cells than in arrested cells in confluence. The expression of topoisomerase IIα increases during the S phase of the cell cycle, reaching a maximum at the end of phase G2/M (Goswami et al., 1996), the level of messenger RNA being ten times higher at the end of phase S than during phase G1. Also, there seems to be a coupling between the synthesis and degradation of topoisomerase IIα and chromosomal condensation/decondensation (Heck et al., 1988).

Present knowledge concerning control of the gene of topoisomerase IIα, all in all, remains rather scanty. Recently, a promoter region of about 650 base pairs has been described by Hockhauser et al. (1992), it has all the characteristics of a domestic gene, an absence of TATA box and a moderate content of GC sites (notably the presence of a Sp1 box which may replace the TATA box) are two examples of this. The presence of 5 inverted CCAAT boxes or ICBs is another feature of this type of promoter.

Transcription factors interacting with the promoter of the gene of human topoisomerase IIα have been described; c-myb (Brandt et al., 1997), p53 (Sandri et al., 1996), ATF (Lim et al., 1998), Sp1 and Sp3 (Kubo et al., 1995) may be mentioned. Whatever the case, apart from NF-Y (also called CBF, ACF and CP1, references in Isaacs et al., 1996), the transcription factors which act on the ICB sequences of the promoter for the gene of human topoisomerase IIα have not yet been identified and characterized; Herzog and Zwelling (1997) have however revealed two proteins with an apparent molecular weight of 90 kD and 140 kD which bind ICB1 to ICB4 and ICB5, respectively. Isaacs and his collaborators (1996) have suggested that NFY as well as another unidentified protein recognize an ICB box of the promoter region of the gene of topoisomerase IIα; they have also shown that ICB2 mutations completely suppressed the reduction in promoter activity normally observed in cells arrested in confluence (Isaac et al., 1996). They identified NFY as a component of a complex induced by the proliferation and which binds in vitro to the ICN2 sequence of the promoter of the gene of human topoisomerase IIα, although NF-Y is always detectable in cells arrested in confluence (Isaacs et al., 1996). They suggested that ICB2 acts as a negative regulator of the promoter of the gene of topoisomerase IIα of cells arrested in confluence and that this repression may be suppressed in proliferative cells. The ICB2 box of the promoter of the gene of topoisomerase IIα therefore plays a primordial role in the arrest of the normal proliferative process when the cells reach confluence.

Transcription factors binding to the ICB sequence as well as the ICB sequence itself therefore form molecular targets for controlling the expression rate of topoisomerase IIα. By intervening on these factors, controlling the expression of the gene of topoisomerase IIα and cell proliferation consequently may be contemplated.

The object of the present invention is to detect new transcription factors binding to the ICB box involved in the control of cell proliferation.

A recent technique called a "simple hybrid" system has been used, which allows DNAc clones coding for the proteins binding to this specific DNA of certain sequences to be isolated. This system has a double advantage as it is able not only to reveal DNA-protein interaction in vivo in yeast, but also to give direct access to complementary DNAs (cDNA) coding for the candidate proteins having a transcription factor activity. This system is mainly based on the construct of a test yeast strain according to the principle developed by Wang and Reed (1993). This yeast strain enables DNAc banks to be screened by demonstrating DNA-protein interaction in vivo through activation of a reporter gene integrated within the genome of the test yeast.

BRIEF SUMMARY OF THE INVENTION

The object of the present invention is therefore an isolated polypeptide designated as ICBP90 (inverted CCAAT box binding protein) with the amino acid sequence SEQ ID No.2. This sequence comprises:

a) a "ubiquitin" domain comprising the sequence of amino acids 1–75 of sequence SEQ ID No.2;

b) a "zinc finger" domain of the C4HC3 type comprising the sequence of amino acids 310–366 of sequence SEQ ID No. 2 and a "zinc finger" domain of the C3HC4 type comprising the sequence of amino acids 724–763 of sequence ID No.2;

c) a presumed "zipper leucine" domain comprising the sequence of amino acids 58–80 of sequence SEQ ID No.2;

d) two potential nuclear localization domains comprising the sequences of amino acids 581–600 and 648–670 of sequence SEQ ID No.2;

e) a site for phosphorylation with a tyrosine kinase comprising the sequence of amino acids 452–458 of sequence SEQ ID No.2;

f) sites for phosphorylation with a dependent cAMP/cGMP protein kinase comprising the sequences of amino acids 246–249, 295–298 and 648–651 of sequence SEQ ID No.2;

g) sites for phosphorylation with a casein kinase II comprising the sequence of amino acids 23–36, 57–60, 91–94, 109–112, 165–168, 265–268, 354–357 and 669–672 of sequence SEQ ID No.2;

h) sites for phosphorylation with a protein kinase C comprising the sequence of amino acids 82–84, 104–106, 160–162, 173–175, 251–253, 301–303, 380–382, 393–395, 504–506, 529–531, 625–627 and 639–641 of sequence SEQ ID No.2.

The present invention also relates to an isolated polypeptide characterized in that, it comprises a polypeptide selected from:

a) a polypeptide of sequence SEQ ID No.2, SEQ ID No.4, SEQ No.6 or SEQ ID No.8;

b) a polypeptide, a polypeptide variant of sequences of amino acids defined under a);

c) a polypeptide homologous to the polypeptide defined under a) or b) and including at least 80% homology, preferably 90% with said polypeptide of a);

d) a fragment of at least 5 consecutive amino acids of a polypeptide defined under a), b) or c);

e) a biologically active fragment of a polypeptide defined under a), b) or c).

BRIEF DESCRIPTION OF THE SEVERAL VIEWS OF THE DRAWINGS

FIG. 6 illustrates nucleotide sequence of ICBP90 (nucleotide sequence SEQ ID NO. 1).

FIG. 7 illustrates protein sequence of ICBP90 (amino acid sequence SEQ ID NO. 2).

FIGS. 9a–b illustrates structural organization of the ICBP 90 gene. FIG. 9B is sequence of the 5' flanking region of the ICBP gene (SEQ ID NO. 12).

FIG. 11 illustrates Northern and Western blot analysis of the expression of ICBP90.

DETAILED DESCRIPTION OF INVENTION

Figure 1:
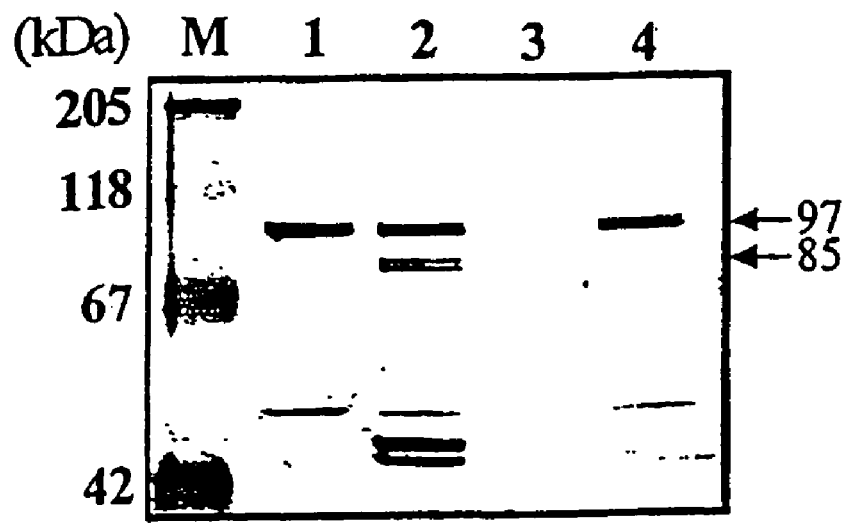
FIG. 1 illustrates the expression of protein ICBP90 in HeLa cells (tumor cells) and in pulmonary fibroblasts in primary culture (non-tumoral cells).

It should be understood that the invention relates to polypeptides obtained through purification from natural sources or else obtained through genetic recombination or even by chemical synthesis and they may then include non natural amino acids.

In the present specification, the term "polypeptide" will be used for also designating a protein or a peptide.

The term "polypeptide variant" shall be understood as designating all the mutated polypeptides which may exist in nature, in particular in the human being, and which notably correspond to truncations, substitutions, deletions and/or additions of amino acid residues. The homologous polypeptides according to the invention at least retain a domain selected from the DNA binding domain and/or the interaction domain with another protein.

It shall be understood that the term "homologous polypeptide" designates polypeptides having certain modifications, as compared with the natural polypeptide ECBP90, as in particular a deletion, addition or substitution of at least one amino acid, a truncation, an extension and/or a chimeric fusion. Among the homologous polypeptides, those for which the sequence of amino acids have at least 80% homology, preferably 90%, more preferably 95%, and most preferably 97% homology with the sequences of amino acids of the polypeptides according to the invention, are preferred. In the case of a substitution, one or several consecutive or non consecutive amino acids are replaced with "equivalent" amino acids. Here, the expression "equivalent" amino acid aims at designating any amino acid capable of being substituted for one of the amino acids of the basic structure without however changing the essential functional properties or characteristics, such as their biological activities, of the corresponding polypeptides such that induction in vivo of antibodies capable of recognizing the polypeptide for which the amino acid sequence is comprised within the amino acid sequence SEQ ID No.2, or in one of its fragments as defined above, and notably the sequence of amino acids SEQ ID No.4, SEQ ID No.6 and SEQ ID No.8. These equivalent amino acids may be determined either by relying on their structural homology with the amino acids which they replace, or on the results of cross biological activity tests which may take place for the different polypeptides. As an example, the possibilities of substitutions which may carried out without their resulting a deep change in the biological activities of the corresponding modified polypeptides will be mentioned, for example replacements of leucine with valine or isoleucine, of aspartic acid with glutamic acid, of glutamine with asparagine, of arginine with lysine etc., the reverse substitutions may naturally be contemplated under the same conditions.

It shall be understood that the term "biologically active fragment" designates in particular a fragment of an amino acid sequence of a polypeptide according to the invention having at least one of the functional characteristics or properties of the polypeptides according to the invention, notably in that: (i) it is capable of being recognized by a specific antibody of a polypeptide according to the invention; (ii) it has at least one of the domains or regions as defined above; (iii) it is capable of binding to DNA and notably to the CCAATT and/or inverted CCAAT boxes; (iv) it is capable of modulating the expression rate of the gene of topoisomerase IIα, (v) it is capable of modulating cell proliferation.

It is understood that the term "polypeptide fragment" designates a polypeptide including a minimum of 5 amino acids, preferably 7 amino acids, more preferably 10, and most preferably 15 amino acids. Fragments of a polypeptide according to the invention, obtained by cleaving said polypeptide with a proteolytic enzyme, with a chemical reagent, or even by placing said polypeptide in a very acid environment, are also part of the invention.

The polypeptide according to the invention may also be associated with other polypeptides through protein—protein interactions. It is understood that the term "protein—protein interactions" designate associations which directly bring into contact at least two proteins. Thus, the polypeptide of the invention may dimerize in order to form homodimers or heterodimers, or be associated as homomultimers or heteromultimers. The polypeptide according to the invention may also interact with another polypeptide in order to exert its action; hence, the polypeptide according to the invention may also have, in addition to its DNA binding domain, a domain acting on the transcription which exerts its action via protein—protein interactions with other protein components of the transcriptional machinery. It is understood that the term "protein component of the transcriptional machinery" designates all transcription factors required for performing and controlling the transcription reaction.

The polypeptide according to the invention is characterized in that it is capable of binding to a DNA sequence and in that it includes at least a DNA binding domain selected from the group consisting of a "zinc-finger" domain and a "leucine zipper" domain; the DNA sequence to which binds said polypeptide is a CCAAT box, preferably an inverted CCAAT box: ICB.

It is understood that the term "binding to a DNA sequence", designates a specific interaction between the polypeptide of the invention and a DNA sequence by means of a series of weak bonds formed between the amino acids of the protein and the bases. The polypeptide according to the invention, has at least a DNA binding domain which contains at least one of the known protein units capable of interacting with DNA, i.e. the zinc-finger structure with which is associated a zinc atom (zinc-finger) the helix-turn-helix structure, the helix-loop-helix structure, and the leucine-zipper structure.

It is understood that the term "zinc-finger unit" designates a sequence of about twenty amino acids assuming a zinc-finger shape in space. There are two types of them: those which contain four cysteines (C4) and those which contain two cysteines and two histidines (C2H2). These amino acids define the nature of the zinc-finger and they are located at its base and a $Zn^{++}$ ion is located in the middle of the square formed by these four amino acids. The polypeptide according to the invention potentially has two units of type C4.

It is understood that the term "leucine zipper type units" designates units belonging to dimeric transcription factors which are either homodimers or heterodimers. The monomer consists of a sequence with a basic character which interacts with DNA in a specific way and of a α helix hydrophobic domain which interacts with the homologous domain of the other chain. In this domain, leucine is found every 7 amino acids, i.e. at each turn of the helix. All these leucines are aligned and the interaction occurs at their level between both monomers. The polypeptide according to the invention potentially has a leucine zipper type unit.

The invention also relates to an isolated polynucleotide characterized in that it codes for a polypeptide of sequence SEQ ID No.1 as defined earlier. Preferably, the polynucleotide according to the invention has the SEQ ID No.1 sequence.

The invention also relates to the isolated polynucleotide characterized in that it comprises a polynucleotide selected from:

a) a polynucleotide with sequence SEQ ID No.1, SEQ ID No.3, SEQ ID No.5 or SEQ ID No.7 or for which the sequence is that of the RNA corresponding to sequence SEQ ID No.1, SEQ ID No.3, SEQ No.5 or SEQ ID No.7;

b) a polynucleotide for which the sequence is complementary to the sequence of a polynucleotide defined under a), c) a polynucleotide for which the sequence includes at least 80% homology with a polynucleotide defined under a) or b), d) a polynucleotide which hybridizes under high stringency conditions with a polynucleotide sequence defined under a), b) or c), e) a fragment of at least 15 consecutive nucleotides, preferably 21 consecutive nucleotides, and more preferably 30 consecutive nucleotides of a polynucleotide defined under a), b), c) or d), except for human EST AI084125, except for the sequence corresponding to sequence SEQ ID No.944 published on Aug. 5th 1999 in Patent Application WO 99 38972 and except for sequences SEQ ID No.9, No.10 and No.11 corresponding to the human ESTs No. AI 0830773, No. AA 811055, No. AA 488 755, No. AA 129 794 and No. AA 354 253 present in the human EST data bases (human dbest), respectively.

In the present specification, it is understood that the terms, "polynucleotide, oligonucleotide, polynucleotide sequence, nucleotidic sequence, or nucleic acid", shall designate a DNA fragment, as well as a double strand DNA, a single strand DNA, as well as transcription products of said DNAs, and/or an RNA fragment, said isolated natural or synthetic fragments whether including non-natural nucleotides or not, designating a specific chaining of nucleotides, whether modified or not, providing definition of a fragment or a region of a nucleic acid.

It is understood that the term "polynucleotide" with a complementary sequence, designates any DNA for which the nucleotides are complementary to those of SEQ ID No.1, SEQ ID No.3, SEQ ID No.5, SEQ ID No.7 or of a part of SEQ ID No.1, SEQ No.3, SEQ ID No.5, SEQ ID No.7 and for which the orientation is inverted.

In the sense of the present invention, it is understood that the term "homology percent" designates a percentage of identity between bases of two polynucleotides, this percentage being purely statistical and the differences between both polynucleotides are randomly distributed throughout their length. According to the invention, the polynucleotides with a homologous nucleic sequence have a homology rate of at least 80%, preferably 90%, more preferably 95%, most preferably 97%.

Hybridization under strong stringency conditions means that the temperature and ionic force conditions are selected in such a way that hybridization between two complementary DNA fragments may be maintained. As an illustration, strong stringency conditions of the hybridization step for the purpose of defining the polynucleotidic fragments described above, advantageously are the following:

DNA—DNA or DNA-RNA hybridization is achieved in two steps: (1) prehybridization at 42° C. for 3 hours in phosphate buffer (20 mM pH 7.5) containing 5×SSC (1×SSC corresponds to a 0.15 M NaCl+0.015 M sodium citrate solution), 50% formamide, 7% sodium dodecylsulfate (SDS), 10× Denhard's, 5% dextran sulfate and 1% salmon sperm DNA; (2) the actual hybridization for 20 hours at a temperature depending on the size of the probe (i.e. 42° C., for a probe with a size>100 nucleotides), followed by two washings for 20 minutes at 20° C. into 2×SSC+2% SDS, one washing for 20 minutes at 20° C. into 0.1×SSC+0.1% SDS. The last washing is performed in 0.1×SSC+0.1% SDS for 30 minutes at 60° C. for a probe with a size>100 nucleotides. The strong stringency hybridization conditions described above, for a polynucleotide with a defined size, will be adapted by one skilled in the art for oligonucleotides with a larger or smaller size, according to the teaching of Sambrook et al., 1989.

Advantageously, a nucleotidic fragment meeting the earlier definition will have at least 15 consecutive nucleotides, preferably at least 21 nucleotides, and even more preferably at least 30 consecutive nucleotides of the sequence from which it stems.

It is understood that the term EST ("expressed sequence tag") designates expressed sequences, characterized in a complementary DNA bank (DNAc) and used as a map marker for genomic DNA.

According to one embodiment of the invention, the polynucleotide according to the invention is characterized in that it is directly or indirectly labeled with a radioactive compound or a non-radioactive compound. Use of a polynucleotide according to the invention as a primer for amplifying or polymerizing nucleic sequences; the invention also relates to the use of a polynucleotide according to the invention as a probe for detecting nucleic sequences. According to the invention, the polynucleotide fragments may be used as a probe or as a primer in methods for detecting, identifying, dosing and amplifying nucleic sequences, and they have a minimum size of 9 bases, preferably 18 bases, and more preferably 36 bases. Finally, the invention is related to the use of a polynucleotide according to the invention as a sense or anti-sense nucleic acid sequence for controlling the expression of the corresponding protein product.

The non-labeled sequences of polynucleotides according to the invention may directly be used as a probe, a primer or an oligonucleotide; however the used sequences are generally labeled for obtaining usable sequences for many applications. The labeling of primers, probes, oligonucleotides according to the invention is achieved through radioactive elements or through non-radioactive molecules; $^{32}P$, $^{33}P$, $^{35}S$, $^{3}H$, or $^{125}I$ may be mentioned among the used radioactive isotopes. The non-radioactive entities are selected from ligands such as biotin, avidin, streptavidin, dioxygenin, haptenes, dyes, luminescent agents, such as radioluminescent, chemiluminescent, bioluminescent, fluorescent, phosphorescent agents.

The polynucleotides according to the invention may thus be used as a primer and/or a probe in methods notably implementing the PCR (polymerase chain reaction) technique (Erlich, 1989; Innis et al., 1990, and Rolfs et al., 1991). This technique requires the selection of pairs of oligonucleotidic primers framing the fragment which should be amplified. Reference may for example, be made to the technique described in the U.S. Pat. No. 4,683,202. The amplified fragments may be identified, for example after agarose gel or polyacrylamide electrophoresis or after a chromatographic technique like gel filtration or ion exchange chromatography. The specificity of the amplification may be controlled by molecular hybridization by using as a probe, nucleotidic sequences of polynucleotides of the invention, plasmids containing these sequences or their amplification products. Amplified nucleotidic fragments may be used as reagents in hybridization reactions in order to demonstrate the presence, in a biological sample, of a target nucleic acid with a sequence complementary to that of said amplified nucleotidic fragments.

The invention is also directed to nucleotidic fragments which may be obtained through amplification by means of primers according to the invention.

Other techniques for amplifying the target nucleic acid may advantageously be used as an alternative to PCR (PCR-like) by means of a pair of primers for nucleotidic sequences according to the invention. It is understood that the term "PCR-like" designates all methods implementing direct or indirect reproductions of nucleic acid sequences, or else those in which the labeling system has been amplified, of course these techniques are known, generally this deals with DNA amplification by a polymerase; when the original sample is an RNA, a reverse transcription should be performed beforehand. Presently, there are very many methods which provide such amplification, such as for example, the SDA (Strand Displacement Amplification) technique (Walker et al., 1992), the TAS (Transcription-based Amplification System) technique described by Kwoh et al., in 1989, the 3SR (Self-Sustained Sequence Replication) technique described by Guatelli et al., in 1990, the NASBA (Nucleic Acid Sequence Based Amplification) technique described by Kievitis et al., in 1991, the TMA (Transcription Mediated Amplification) technique, the LCR (Ligase Chain Reaction) technique described by Landegren et al., in 1988, and enhanced by Barany et al., in 1991, which uses a thermostable ligase, the RCR (Repair Chain Reaction) technique described by Segev in 1992, the CPR (Cycling Probe Reaction) technique described by Duck et al., in 1990, the Q-beta-replicase amplification technique described by Miele et al., in 1983, and notably enhanced by Chu et al., in 1986 and Lizardi et al., in 1988, and then by Burg et al., as well as Stone et al., in 1996.

If the target polynucleotide is an RNA, for example a RNAm, a reverse transcriptase type enzyme will advantageously be used before implementing an amplification reaction with the primers according to the invention or before implementing a detection method with probes of the invention, in order to obtain a DNAc from the RNA contained in the biological sample. The obtained DNAc will then be used as a target for the primers or the probes implemented in the detection or amplification method according to the invention.

The nucleotidic probes according to the invention, specifically hybridize with a DNA or RNA polynucleotide molecule according to the invention, more particularly with the sequence SEQ ID No.1 coding for the ECBP90 polypeptide, under strong stringency hybridization conditions such as those given as an example earlier.

The hybridization technique may be used in different ways (Matthews et al., 1988). The most general method consists of immobilizing the nucleic acid extracted from cells of different tissues or from cells cultivated on a support (such as nitrocellulose, nylon, polystyrene) and of incubating, under well defined conditions, the immobilized target nucleic acid with the probe. After hybridization, the probe excess is removed and the formed hybrid molecules are detected by the suitable method (measurement of radioactivity, fluorescence or enzyme activity related to the probe).

According to another embodiment of the nucleic probes, according to the invention, the latter may be used as a capture probe. In this case, a so-called "capture probe" is immobilized on a support and is used for capturing through specific hybridization, the target nucleic acid obtained from the biological sample to be tested and the target nucleic acid is then detected by a second probe, a so-called "detection probe", labeled with an easily detectable element.

In a preferred embodiment, the invention comprises the use of a sense or anti-sense oligonucleotide for controlling the expression of the corresponding protein product. Among the interesting nucleic acid fragments, anti-sense oligonucleotides i.e. those for which the structure provides an inhibition of the expression of the corresponding product, by hybridization with the target sequence, may be mentioned in particular. The sense oligonucleotides which, through interaction with the proteins involved in the control of the expression of the corresponding product which will induce either an inhibition, or an activation of this expression, should also be mentioned. The oligonucleotides according to the invention, have a minimum size of 9 bases, preferably 18 bases, and more preferably 36 bases.

The invention relates to a recombinant vector for cloning a polynucleotide according to the invention and/or for expressing a polypeptide according to the invention characterized in that, it contains a polynucleotide according to the invention, as described earlier. The vector according to the invention, is characterized in that it includes components for the expression, possibly the secretion, of said sequences in a host cell. These vectors are useful for transforming host cells in order to clone or express nucleotidic sequences of the invention. Particular vectors are for examples the vectors of plasmidic or viral origin. Among these vectors, those of the pGEX series (Pharmacia) for expression in bacteria or pSG5 (Stratagene, La Jolla, Calif. USA) are preferred for expression in a eukaryotic system.

According to a particular embodiment, the vector according to the invention includes components for controlling expression of the polypeptides, these control components are preferably selected from (i) the promoter sequence of the ICBP90 gene according to the invention which corresponds to sequence SEQ ID No.12; (ii) a polynucleotide for which the sequence is complementary to the sequence SEQ ID No.12; (iii) a polynucleotide for which the sequence includes at least 80% identity with a polynucleotide as defined in (i) or (ii); (iv) a polynucleotide which hybridizes under strong stringency conditions with the polynucleotide sequence defined under (i), (ii), (iii). Computer tools available to one skilled in the art will easily allow him/her to identify the required and sufficient promoter control boxes for controlling the genic expression, notably the TATA, CCAAT, GC boxes, as well as enhancer or silencer control sequences which control in CIS the expression of genes according to the invention.

The use of the above components defined and selected from the sequence SEQ ID No.12 for controlling the expression of heterologous polypeptides other than those of the invention and notably for controlling the expression of heterologous polypeptides in cell types in which the polypeptides according to the invention are expressed normally, is also within the scope of the invention.

The invention further comprises host cells, notably eukaryotic and prokaryotic cells, characterized in that they are transformed with vectors according to the invention. Preferably, the host cells are transformed under conditions allowing a recombinant polypeptide according to the invention to be expressed. The cell host may be selected from bacterial cells (Olins and Lee, 1993), but also from yeast cells (Buckholz, 1993), as well as animal cells, in particular mammal cell cultures (Edwards and Aruffo, 1993), but also insect cells wherein methods implementing baculoviruses for example may be used (Luckow, 1993). These cells may be obtained by introducing into the host cells a nucleotidic sequence inserted in a vector such as defined above, and then by growing said cells under conditions providing replication and/or expression of the transfected nucleotidic sequence.

The invention also relates to a method for preparing a polypeptide, characterized in that it implements a vector according to the invention. More specifically, the invention relates to a method for preparing a recombinant polypeptide characterized in that the transformed cells according to the invention are grown under conditions providing expression of said recombinant polypeptide and in that said recombinant polypeptide is recovered.

The polypeptide according to the invention may be obtained according to a method of the invention, and according to production techniques for recombinant polypeptides, known to one skilled in the art. The present invention therefore relates to the recombinant polypeptide which may be obtained by the method shown above. In this case, the nucleic acid sequence used is placed under the control of signals providing its expression in a cell host. An efficient production system for a recombinant polypeptide requires the availability of a vector, for example of plasmidic or viral origin and of a compatible host cell. The vector should include a promoter, signals for initiating and terminating the translation, as well as suitable regions for controlling the transcription. It should be able to be maintained in the cell stably and may optionally have particular signals specifying the secretion of the translated polypeptide. These different control signals are selected depending on the used host cell. For this purpose, the nucleic acid sequences according to the invention may be inserted in autonomous replication vectors inside the selected host or integrative vectors of the selected host. Such vectors are prepared according to methods currently used by one skilled in the art and the resulting clones may be introduced into a suitable host by standard methods such as for example transfection with calcium phosphate precipitation, lipofection, electroporation, thermal shock.

The recombinant polypeptides obtained as indicated above, may both exist in the glycosylated and non-glycosylated form and may have the natural tertiary structure or not.

The polypeptides obtained through chemical synthesis and which may include non-natural amino acids corresponding to said recombinant polypeptides, are also comprised in the invention. The peptides according to the invention may also be prepared by conventional techniques, in the field of peptide synthesis. This synthesis may be carried out in a homogenous solution or in the solid phase.

The methods used for purifying recombinant polypeptides are well known to one skilled in the art. The recombinant polypeptide may be purified from lysats and cell extracts, from the supernatant of the culture medium, by methods either used individually or in combination, such as fractionation, chromatography methods, immuno-affinity techniques by means of specific mono- or polyclonal antibodies, etc.

A preferred alternative consists of producing a recombinant polypeptide fusioned to a "carrier" protein (chimeric protein). The advantage of this system is that it provides stabilization and a reduction in the proteolysis of the recombinant product, an increase in the solubility during renaturation in vitro and/or a simplification of the purification when the fusion partner has an affinity for a specific ligand.

The invention also relates to a monoclonal or polyclonal antibody and to its fragments, characterized in that they specifically bind a polypeptide according to the invention. Chimeric antibodies, humanized antibodies and simple chain antibodies are also part of the invention. Antibody fragments according to the invention are preferably Fab or F(ab')2 fragments.

The polypeptides according to the invention allow monoclonal or polyclonal antibodies to be prepared. Advantageously, monoclonal antibodies may be prepared from hybridomas according to the technique described by Kohler and Milstein in 1975. The inventors use this technique for obtaining a hybridoma producing a new highly specific monoclonal antibody of an epitope of protein ICBP90.

Polyclonal antibodies may be prepared, for example, by immunizing an animal, for example a mouse, with a polypeptide according to the invention associated with an adjuvant from the immune response, and then by purifying the specific antibodies contained in the serum of the immunized animals on an affinity column on which is fixed beforehand the polypeptide which has been used as an antigen. The polyclonal antibodies according to the invention may also be prepared by purification on an affinity column, on which a polypeptide according to the invention has been immobilized beforehand.

The invention also relates to a specific monoclonal antibody of the human ICBP90 protein and capable of inhibiting interaction between ICBP90 and the DNA sequence onto which protein ICBP90 specifically binds. According to another embodiment, the monoclonal antibody according to the invention and specific to the human ICBP90 protein is capable of inhibiting the interaction between ICBP90 and the proteins with which interacts ICBP90, said proteins preferably being ICBP90 itself, or proteins from the transcriptional complex. It is understood that the term "proteins from the transcriptional complex" designates all proteins participating in the transcription reaction whether this happens in the initiation, elongation, or termination of the transcription.

The antibodies of the invention may also be labeled in the same way as described earlier for the nucleic probes of the invention, and preferably with an enzymatic, fluorescent or radioactive type labeling.

Moreover, in addition to their use for purifying polypeptides, the antibodies of the invention, in particular the monoclonal antibodies, may also be used for detecting these polypeptides in a biological sample.

They thus form a means for analyzing the expression of the polypeptide according to the invention, for example through immunofluorescence, labeling with gold, enzymatic immunoconjugates.

More generally, the antibodies of the invention may advantageously be implemented in any situation where the expression of a polypeptide according to the invention needs to be observed, and more particularly in immunocytochemistry, in immunohistochemistry, or in Western blotting experiments.

Thus, the invention relates to a method for detecting and/or dosing a polypeptide according to the invention, in a biological sample, characterized in that it comprises the following steps for bringing the biological sample into contact with antibodies according to the invention and then for detecting the formed antigen-antibody complex. This method may be used in immunocytochemistry for cell localization of the polypeptide according to the invention and in immunohistochemistry for assessing cell proliferation.

A kit for detecting and/or dosing a polypeptide according to the invention in a biological sample, is also within the scope of the invention, characterized in that it comprises the following components: (i) a monoclonal or polyclonal antibody such as described earlier; (ii) if necessary, the reagents for forming the favorable medium for the immunological reaction; (iii) the reagents for detecting the antigen-antibody complexes produced by the immunological reaction. This kit is notably useful for conducting Western blotting experiments; with the latter, control of the expression of the polypeptide according to the invention may be investigated starting with tissues or cells. This kit is also useful for immunoprecipitation experiments in order to notably detect proteins which interact with the polypeptide according to the invention.

Any conventional procedure may be implemented for carrying out such a detection and/or dosage. As an example, a preferred method involves immunoenzymatic processes according to the immunofluorescence or radioimmunological (RIA) ELISA technique or equivalent.

The invention also comprises a method for detecting and/or dosing a nucleic acid according to the invention, in a biological sample, characterized in that it includes the following steps: (i) isolation of the DNA from the biological sample to be analyzed, or obtaining a DNAc from the RNA of a biological sample; (ii) specific amplification of the DNA coding for the polypeptide according to the invention by means of primers; (iii) analysis of the amplification products.

The invention further comprises a kit for detecting and/or dosing a nucleic acid according to the invention, in a biological sample, characterized in that it comprises the following components: (i) a pair of nucleic primers according to the invention, (ii) the required reagents for carrying out a DNA amplification reaction and optionally (iii) a component for checking the sequence of the amplified fragment, more particularly a probe according to the invention.

The invention also comprises a method for detecting and/or dosing a nucleic acid according to the invention, in a biological sample, characterized in that it includes the following steps: (i) bringing a probe according to the invention into contact with a biological sample; (ii) detecting and/or dosing the hybrid formed between said probe and the DNA of the biological sample.

The invention also comprises a kit for detecting and/or dosing a nucleic acid according to the invention, in a biological sample, characterized in that it comprises the following components: (i) a probe according to the invention, (ii) the reagents required for implementing a hybridization reaction and if necessary, (iii) a pair of primers according to the invention, as well as the reagents required for an DNA amplification reaction.

The invention particularly relates to methods according to the invention and described above, for detecting and diagnosing cell proliferation, and more particularly cell proliferation of cancerous origin.

The invention also relates to a method for screening ligands able to affect the transcriptional activity of a gene, the promoter of which includes CCAAT and/or inverted CCAAT boxes capable of binding a polypeptide according to the invention, said method being characterized in that it includes the following steps for bringing into contact said polypeptide and one or several potential ligands in the presence of reagents required for implementing a transcription or detection reaction and/or a reaction for measuring transcriptional activity. One of the objects of the invention is also to provide a kit or package for screening ligands able to affect the transcriptional activity of a gene, the promoter of which includes CCAAT and/or inverted CCAAT boxes capable of binding a polypeptide according to the invention characterized in that it comprises the following components: (i) a polypeptide according to the invention; (ii) a ligand; (iii) the reagents required for implementing a transcription reaction.

The ICBP90 polypeptide according to the invention has a nuclear receptor function. It is understood that the term "nuclear receptor" designates a polypeptide which has the essential properties of hormone nuclear receptors. This gene superfamily contains i.a. the retinoic acid nuclear receptors (RAR, RXR, . . . ), steroid hormone nuclear receptors (glucocorticoids, mineralocorticoids, progesterone, androgen, estrogen), and thyroid hormone nuclear receptors (T3 hormone). Accordingly, one of the objects of the present invention is also to provide a method for screening ligands able to affect the "nuclear receptor" function of the polypeptide according to the invention. Such a method includes the steps of:

a) bringing into contact the polypeptide of the invention and one or several potential ligands in the presence of required reagents;

b) detecting and/or measuring the transcriptional activity of a gene, the promoter of which includes nucleotidic sequences onto which the polypeptide of the invention may be bound. Preferably, said nucleotidic sequences are CCAAT and/or inverted CCAAT boxes (ICB).

Techniques for detecting and/or measuring the transcriptional activity are known to one skilled in the art. The Northern blotting and RT-PCR technologies should notably be mentioned, which may be implemented with polynucleotides of the invention used as a probe or as a primer, respectively.

It is understood that the term "ligand" defines all compounds able to interact with the polypeptide according to the invention, in order to form a complex able to affect the transcriptional activity, i.e. to increase, reduce, modulate or cancel the transcription of a gene under the control of a promoter containing a DNA sequence to which binds the polypeptide of the invention.

Such a ligand is therefore able to have an agonist or antagonist activity. Among the ligands according to the invention, the biological molecules which interact with the polypeptide according to the invention as well as all the synthetic chemical compounds, should be mentioned. Among these ligands, the antibody according to the invention as well as an oligonucleotide having an identity of sequence with the CCAAT and/or inversed CCAAT nucleotidic sequence should also be mentioned; such a ligand is able to form an inhibitor of the polypeptide according to the invention.

The invention also relates to the ligand which may be obtained by the previous screening methods.

It is also understood that the term "ligand" defines any compound able to bind to the binding DNA sequence for the polypeptide according to the invention. Such a ligand forms a competitive inhibitor of the polypeptide according to the invention for its binding to the DNA sequence.

Preferably, the biological sample according to the invention in which detection and dosage is performed, consists of a body fluid, for example human or animal serum, blood, saliva, lung mucus, or biopsies. The biological liquid resulting from a broncho-alveolar washing also obtained during analyses for diagnosing cancers of the deep airways is also included in the definition of a biological sample of the invention.

According to another aspect, the invention relates to a compound characterized in that it is selected from an antibody, a polypeptide, a ligand, a polynucleotide, an oligonucleotide, or a vector according to the invention as a drug, and notably as active ingredients of a drug: these compounds preferably will be in soluble form, associated with a pharmaceutically acceptable carrier. It is understood that the term "pharmaceutically acceptable carrier" designates any type of carrier usually used in preparing injectable compositions, i.e. a diluent, a suspension agent, such as an isotonic or buffered saline solution. Preferably, these compounds will be administered systemically, in particular intravenously, intramuscularly, intradermally, or orally. Their modes of administration, dosages and optimal dosage forms may be determined according to the criteria generally considered in establishing a suitable treatment for a patient as for example, the age or body weight of the patient, the seriousness of his/her general condition, tolerance to the treatment and ascertained secondary effects, etc.

According to another aspect, the invention relates to a compound, characterized in that it is selected from a polypeptide, a polynucleotide, an anti-sense polynucleotide, an antibody, a vector, a cell, a ligand according to the invention as a drug and notably as active ingredients of a drug; these compounds preferably will be in soluble form, associated with a pharmaceutically acceptable carrier. It is understood that the term "pharmaceutically acceptable carrier" designates any type of carrier usually used in preparing injectable compositions, i.e. a diluent, a suspension agent, such as an isotonic or buffered saline solution. Preferably, these compounds are administered systemically, in particular intravenously, intramuscularly, intradermally or orally. Their modes of administration, dosages and optimal dosage forms may be determined according to criteria generally considered in establishing a suitable treatment for a patient such as for example the age or body weight of the patient, the seriousness of his/her general condition, tolerance to the treatment and the ascertained secondary effects, etc. When the agent is a polypeptide, an antagonist, a ligand, a polynucleotide, for example an anti-sense composition, a vector, it may be introduced into tissues or host cells by a number of ways, including viral infection, micro-injection, or fusion of vesicles. Jet injection for an intramuscular administration as described by Furth et al. (1992) may also be used. The polynucleotide may also be deposited on gold micro-particles, and be delivered intradermally by means of a particle bombardment apparatus, or a "gene pistol" as described in the literature (see for example Tang et al. (1992) where gold microprojectiles are coated with the polynucleotide of the invention, preferably the anti-sense polynucleotide of the invention, then are bombarded into the skin cells.

The compound comprising this invention is used for the preparation of a pharmaceutic designed to modulate, raise, or diminish cellular proliferation.

The invention also has at its foundation a pharmaceutical composition that can act in the preventive and curative treatment of cancer and is characterised by a therapeutically effective quantity of an active compound and a pharmaceutically acceptable excipient. Using the preferred method of synthesis, this pharmaceutical composition contains antibodies that serve as targeting agents; those antibodies are conjugated to at least one agent selected from among antiproliferative, antineoplastic, or cytotoxic agents. These agents are either radioisotopes or non-isotopic substances. The conjugation of antibodies contained in the present invention with antiproliferative, antineoplastic, or cytotoxic agents can be utilized for arresting the development of cancers and for inducing regression and even elimination of tumoural masses. Preferably, the antibody or the antibody fragment conjugated to the agent is administered to the cancer patient and delivered to tumour sites by oral or parenteral route through a pharmaceutically acceptable transporting liquid, such as saline. Alternatively, a solution or suspension of antibody and antibody fragment conjugated to an agent can be perfused directly into the tissue of a malignant epithelial cancer, a method used by preference when the cancer has not metastasized.

For therapeutic use, the preferred radioisotopes, conjugated to monoclonal antibodies, are gamma emitters, the most effective being iodine$^{131}$, yttrium$^{90}$, gold$^{199}$, palladium$^{100}$, copper$^{67}$, bismuth$^{217}$, and antimony$^{211}$. Alpha and beta emitting radioisotopes can also be employed for therapy. Non-isotopic substances conjugated to monoclonal antibodies and used for therapy are abundant and varied; for example: (i) antimetabolites, such as anti-folate agents like methotrexate, (ii) purine and pyrimidine analogues (mercaptopurine, fluorouracil, 5-azacytidine, (iii) antibiotics, (iv) lectins (ricin, abrin) and (iv) bacterial toxins (diphtheria toxin).

The antibodies of the invention can also be used as targeting agents to target cytotoxic cells, such as human T cells, monocytes or NK cells present or not at a metastasised tumour site. Antibodies can attach to cytotoxic cells via the Fc receptor situated at the surface of these cells or via an intermediary antibody that has a double specificity. Such bi-specific antibodies for the targeting of cancerous cells can be produced by fusing an immune cell producing the antibody of the present invention or a hybridoma of the present invention with a cell producing an antibody directed against the targeted cytotoxic cell. Bi-specific antibodies can equally be produced by chemically coupling two antibodies having the desired specificity. The antibodies of this invention also permit the targeting of carriers bearing antiproliferative, antineoplastic, or cytotoxic agents to the site of the tumor or metastatic tumor. By carriers we are referring to liposomes and viral particles. In certain cases, it's possible to predetermine the target elements to assure a specific expression in certain tissues or cells and limit the expression zones of the polypeptides of this invention.

The invention also concern a product comprising at least a compound of the invention, and at least an anticancerous agent as a combination product for a simultaneous, separated or delayed use over the time.

In summary, the invention concerns a composition for the detection, localisation, and imaging of cancers, using an antibody that is tagged directly or indirectly by a marker whose signal is generated by radioactive or non-isotopic substances as defined above. The invention also has as objective the localisation and imaging of cancers, including (i) the stages of dispersion after parenteral injection into a human of a composition based on the invention; (ii) the accumulation of tagged antibody, after an adequate time period, at the vicinity of cancer cells, then the penetration of those cells by the tagged antibody without significantly affecting normal cells; (iii) the detection of a signal using an appropriate signal detector; and (iv) the conversion of the detected signal to an image of the cancerous cells.

Other characteristics and advantages of the invention are discussed after this description accompanied by the examples below. In the examples, we will refer to the following figures.

FIG. 1: Expression de la Protein ICBP90 in HeLa Cells (Tumour Cells) and in Pulmonary Fibroblasts in Primary Culture (Non-Tumoral Cells).

The detection of the endogenous protein, ICBP90, was carried out on total protein extracts from confluent (lane 1) and proliferating (lane 2) HeLa cells and on total protein extracts from primary cultures of human pulmonary fibroblasts at confluence (lane 3) and in proliferation (lane 4). After migration in a polyacrylamide gel in the presence of 8% SDS, the proteins were transferred to nitrocellulose membranes by electrotransfer. The revelation of the protein was performed using antibody 1RC1C-10 diluted to 1/4000

(initial concentration 2 mg/ml) and a secondary antibody coupled to alkaline phosphatase and directed against the heavy chains of mouse antibodies. In the lanes corresponding to extracts from HeLa cells, there is a major band at 97 kDa; for proliferating HeLa cells, supplementary bands of sizes less than 97 kDa appear (lane 2). In confluent human pulmonary fibroblasts, the endogenous protein is not expressed (lane 3), while the protein does appear when the cells begin to proliferate (lane 4). These observations suggest that the endogenous ICBP90 protein is a marker of cellular proliferation for normal cells (fibroblasts), whereas for tumour cells, it is a marker regardless of the cellular stage.

Figure 2:
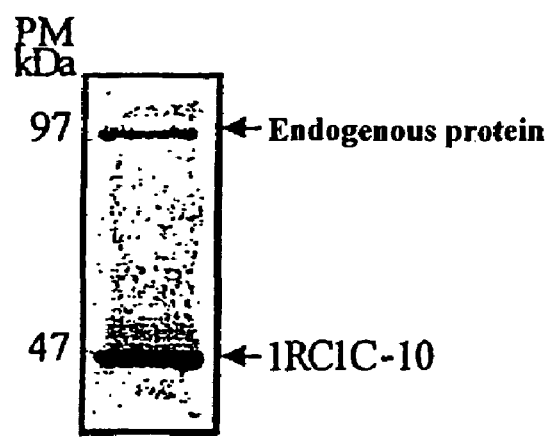
FIG. 2 illustrates immunoprecipitation of the endogenous protein.

FIG. 2: Immunoprecipitation of the Endogenous Protein

Immunoprecipitation was carried out on total protein extracts from MOLT-4 cells. 1RC1C-10 antibodies were attached to the protein beads of G-Sepharose, then put into contact with protein extract for 2 hours at room temperature. After washing, the bead/1RC1C-10/protein complexes were precipitated by centrifugation and analysed by migration in a 8% polyacrylamide gel in the presence of SDS. They were then transferred to nitrocellulose membranes for revelation of the proteins as indicated in FIG. 1. A unique band appears at 97 kDa, as well as a band of 45 kDa corresponding to the heavy chain of 1RC1C-10.

Figure 3:
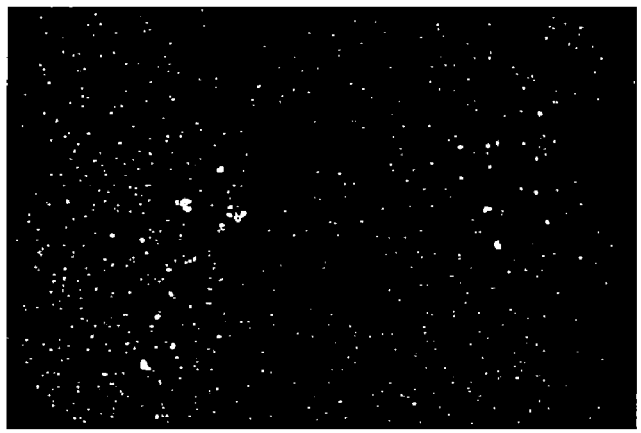
FIG. 3 illustrates nuclear localization of the endogenous protein.

FIG. 3: Nuclear Localisation of the Endogenous Protein

We used HeLa cells to examine the endogenous expression of the protein ICBP90 in situ employing 1RC1C-10 antibody and a secondary anti-mouse antibody coupled to fluorochrome CY3. The fluorescent marker localises exclusively in the nucleus. The nucleolus and the cytoplasm are not labelled.

Figure 4:
FIG. 4 illustrates expression of endogenous ICBP59 in proliferating cells.

FIG. 4: Expression of Endogenous ICBP59 in Proliferating Cells

We observed endogenous protein in paraffin sections of human appendix. After deparaffinization and pre-treatment by heat in acid buffer (unmasking of antigenic sites), the sections were incubated for 16 hours with 1RC1C-10 antibodies diluted 1/10000 (initial concentration of 2 mg/ml). Revelation was performed by adding biotinylated secondary antibody, and then incubating with streptavidine-peroxidase complex. A counter-staining of nuclei by Harris' haematoxylin was also carried out. The labelling by 1RC1C-10 is localised essentially in zones of cellular proliferation. The labelled cells are found in glandular crypts (GC), as well as germinative zones (ger).

FIG. 5: Expression of ICBP-59 in Diverse Human Tissues

Figures 5A, 5B:
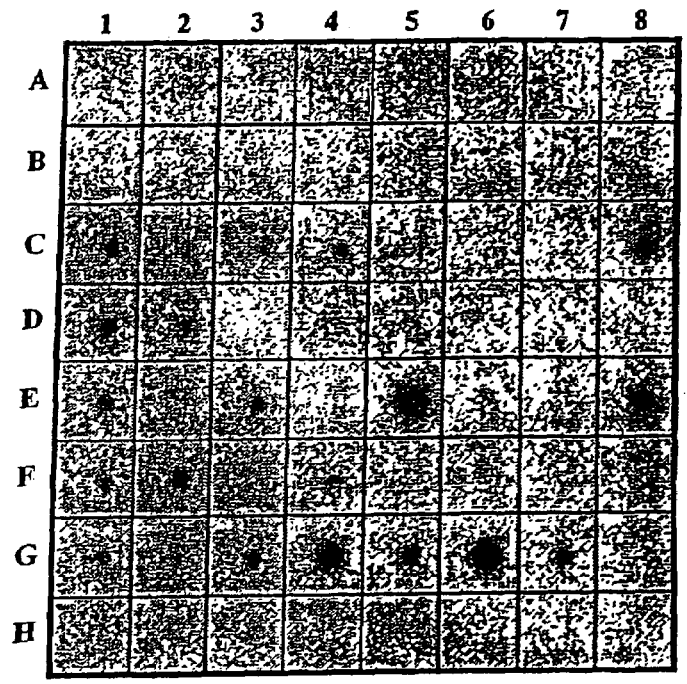
FIG. 5 illustrates expression of ICBP-59 in diverse human tissues.

We evaluated the level of expression of mRNA corresponding to ICBP59 in 50 different human tissues using an RNA dot blot. The blot was hybridised for 16 hours at 68° C. with a cDNA (32P) radioactive probe of 679 bp in ExpressHyb (Clontech) hybridisation solution. After washing several times, we revealed the protein by autoradiography (one week exposure at 80° C.). The tissues demonstrating the highest expression level were foetal and adult thymus, as well as adult bone marrow and foetal liver. FIG. 5a is a graph showing the 50 different human tissues using an RNA dot blot. FIG. 5b is the legend identifying the human tissue represented in the corresponding graph of FIG. 5a.

FIG. 6: Nucleotide Sequence of ICBP90 (Nucleotide Sequence SEQ ID NO. 1).

cDNA coding for ICBP90 (nucleotide SEQ ID NO. 1) measures 2379 bp. The portions of sequence indicated in bold are those that do not appear in the human EST database (human dbest). The other sequences exist in diverse EST:

From 1 to 325: EST no A1083773,

From 367 to 865 EST no AA811055,

From 940 to 1857 EST no AA488755, EST no AA129794, and EST no AA354253.

FIG. 7: Protein Sequence of ICBP90 (Amino Acid Sequence SEQ ID NO.2).

The amino acid sequence of ICBP90 (amino acid sequence SEQ ID NO. 2) was deduced of the nucleotide sequence from FIG. 6 (SEQ ID NO. 1). ICBP (amino acid sequence SEQ ID NO. 2) is composed of 793 residues and has a theoretical molecular weight of 89,758 kDa. The pKi is 7.7. The amino acids indicated in grey correspond to ICBP-59.

Figure 8:
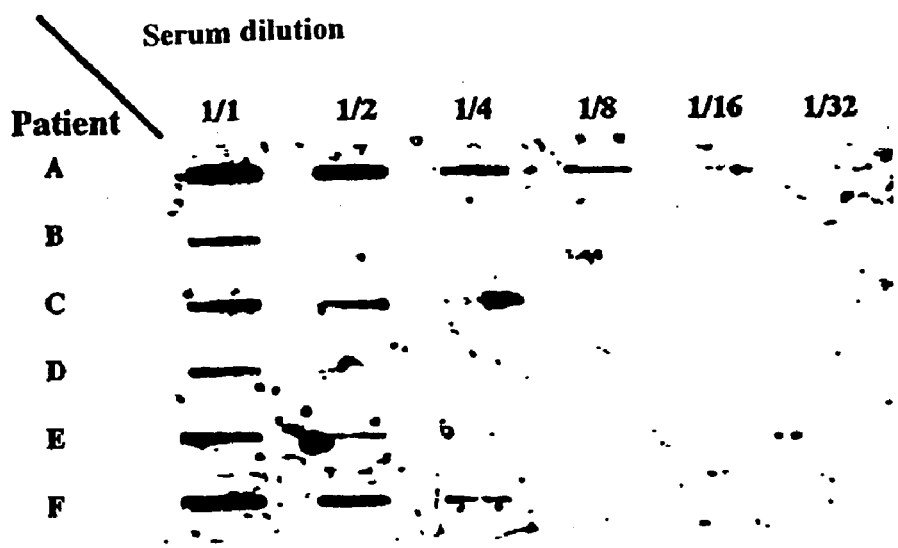
FIG. 8 illustrates detection of ICBP90 in the sera of patients displaying elevated serum markers for solid tumors.

FIG. 8: Detection of ICBP90 in the Sera of Patients Displaying Elevated Serum Markers for Solid Tumours.

A volume of 2 µl of serum from each patient was diluted in 1 ml of PBS (1× Phosphate Buffered Saline) containing 0.1% Tween-20 followed by serial dilutions carried out in the same buffer as indicated in the figure. A 0.5 ml aliquot of each dilution was filtered onto a nitrocellulose membrane using a "Slot Blot BioRad" apparatus. The membrane was then blocked in the presence of PBS buffer (containing 0.1% Tween-20 and 5% milk) for 1 hour at room temperature. The protein ICBP90 was revealed by 1RC-1C10 antibodies (1 ng/ml) and anti-mouse secondary antibodies coupled to peroxidase diluted by 1/5000. The bands were uncovered by chemiluminescence (10 second exposure of X-MAT (Kodak) film).

Figure 9:
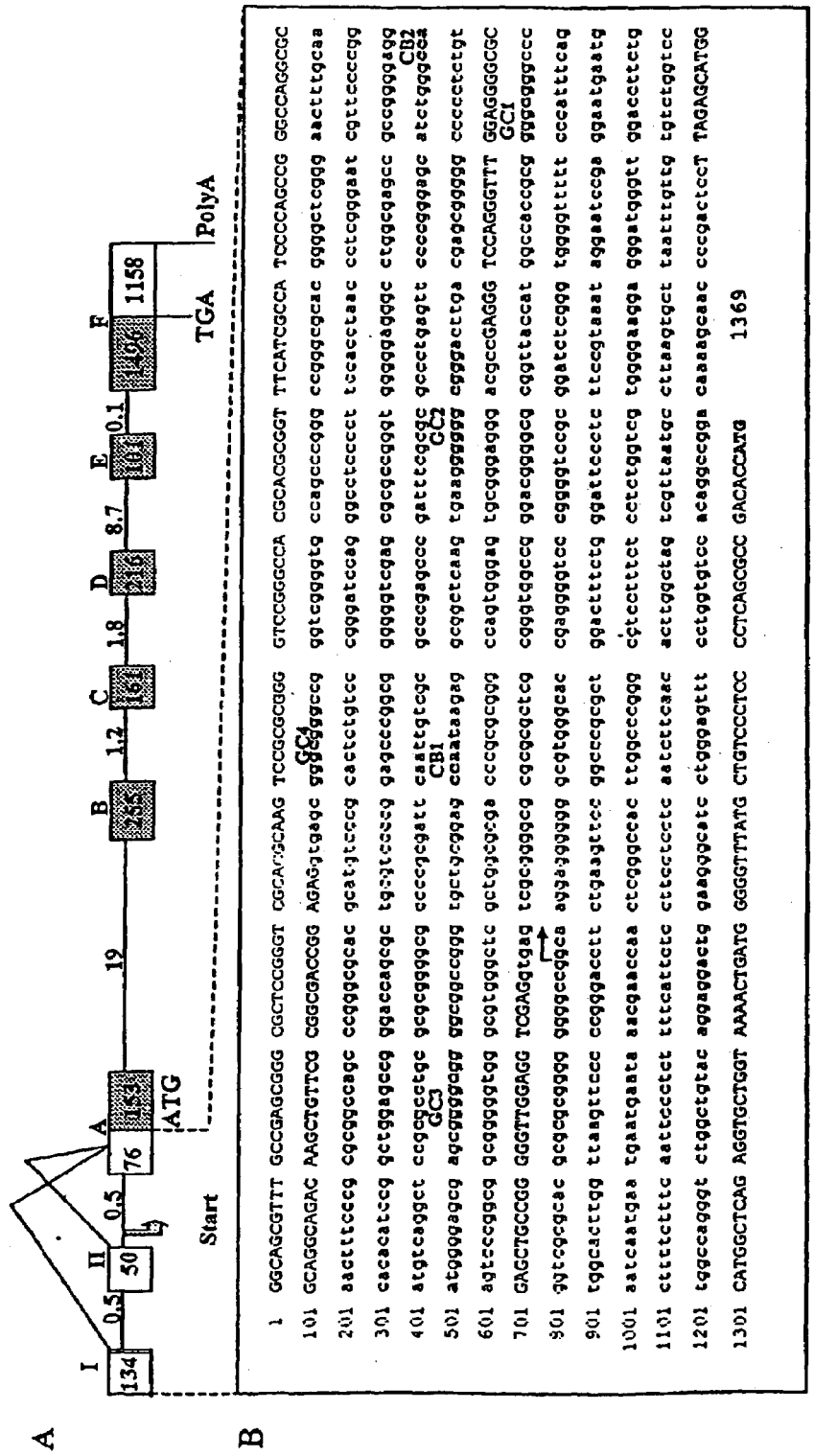
FIG. 9 A. Exons are represented by the boxes: the grey boxes represent coding exons; white boxes represent non-coding exons.

FIG. 9: Structural Organisation of the ICBP90 Gene.

A. Exons are represented by the boxes: the grey boxes represent coding exons; white boxes represent non-coding exons. The size of each exon is indicated in bp in each box, and the names of the exons are above the boxes. Introns are illustrated schematically by fine lines and their approximate sizes are in bp. A putative transcription start site and a polyadenylation consensus signal are indicated. The ATG is the start codon marking the beginning of translation and TGA, the stop codon for the end of translation.

B. Sequence of the 5' flanking region of the ICBP90 gene (Seq ID No 12) (Genbank Accession No AF 220 226 submitted 30 Dec. 1999). The exons are uppercase and the introns are lowercase. The start codon ATG is in bold uppercase, the boxes rich in GC (GC) and the CCAAT (CB) boxes are in bold lowercase.

Figure 10:
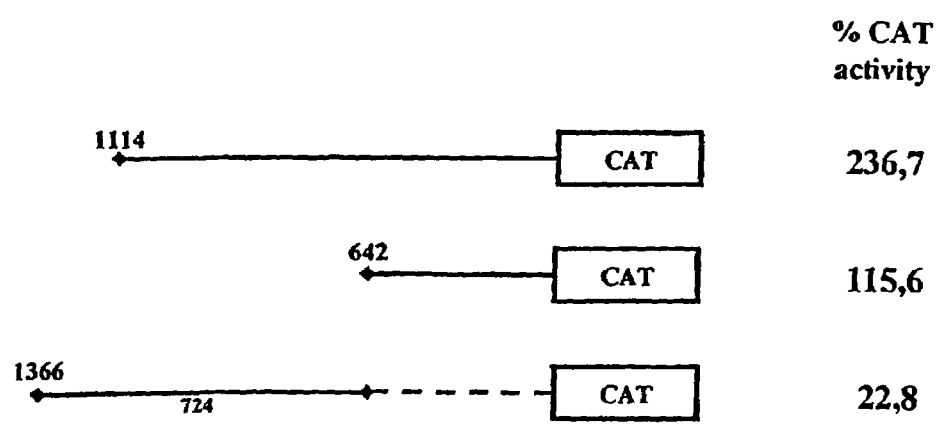
FIG. 10 illustrates analysis of the ICBP promoter.

FIG. 10: Analysis of the ICBP90 Promoter.

The promoter sequence of ICBP90 was ligated to the reporter gene, CAT, contained on the pBLCAT2 vector and subsequently transfected into COS-1 cells.

A schematic representation of the constructions appears on the left, the numbers referring to the nucleotides upstream of the start codon. Relative CAT activity of cellular extracts compared to induction of CAT activity by the minimal TK promoter are expressed in percentage (based on the results of 3 independent transfection experiments) and indicated on the right.

FIG. 11: Northern and Western Blot Analysis of the Expression of ICBP90.

A. Northern hybridisation was performed on a Northern blotting membrane, containing samples of RNA from cell lines of cancers and various organs. A specific probe for ICBP90, synthesized by PCR, and labelled by digoxigenin, was used to detect ICBP90 mRNA. mRNA sizes are noted on the right side of line 7.

Lines 1 through 7 represent RNA from, respectively, leukaemic HL-60 promyelocytes, hela 53 cells K562 cells from chronic myelogenic leukaemia, MOLT-4 lymphoblastic leukaemia cells, Raji cells from Burkitt's lymphoma, SW480 cells from colorectal adenocarcinoma, and A549 cells from pulmonary carcinoma.

The histogram demonstrates the rate of expression of mRNA corresponding to 5.1 kb and 4.3 kb bands by percentage of the rate of mRNA expression of the 5.1 kb band of HL-60 (line 1, FIG. 11A).

B. Western blot analysis of ICBP90 expression in MOLT-4 and HeLa cells.

We prepared total cell lysates from proliferating HeLa and MOLT-4 cell cultures. The expression of ICBP90 was analysed by Western blotting using 1RC1C-10 antibodies.

EXAMPLE 1

Evidence of a New Binding Protein for the ICB Sequence 1.1 Reporter Construction for the Screening of the Library The simple hybrid system is a powerful technique for detecting, in vivo, in yeast the interaction of proteins with specific DNA sequences when screening cDNA libraries. This technique allows you to evaluate directly cDNA corresponding to the protein to be linked. Several studies using this technique resulted in the identification of novel proteins. The protocols are well described by Inouye et al. (1994) and Wang and Reed (1993).

Briefly, the following oligonucleotides have been synthesized:

5'-AATTC GATTGGTTCTGATTGGTTCTGATTGGTTCTT-3' and 5'-CTAGAAGAACCAATCAGAACCAATCA-GAACCAATCG-3'. These nucleotides were then hybridised. According to the documentation of the manufacturer (Clontech, Palo Alto, Calif.), the reporter construct targeted possesses three copies in tandem of the ICB2 sequence (ICB2X3). As mentioned above, one copy of ICB2 is underscored and the CCAAT sequences are in bold. To determine the specificity of protein binding to the ICB box, the following oligonucleotides, containing three copies in tandem of the GC1 box (GC1X3), also present in the promoter, have been synthesized and hybridised:

5'-AATTCGGGGCGGGGCCGGGGCGGGC-CCGGGGCGGGGCT-3' 5'-CTAGAGCCCCGCCCCGGC-CCCGCCCCGGCCCCGCCCCGG-3'

The resulting target DNA fragments were cloned into the polylinker of the pHISi-1 integrative plasmid (Clontech) by cohesive-end ligation to the plasmid's XbaT-EcoRI site, upstream of the minimal promoter of the gene, his3. The yeast strain, YM4271 (Clontech), was used for the transformation. Transformed colonies of yeast containing the plasmid integrated in their genomes were selected by cultivating the yeast in synthetic dropout medium lacking histidine. We isolated two colonies: one for ICB2 and the other for the GC1 box.

1.2 Screening the Library

A cDNA library from the Jurkat cell line, cloned into the EcoRI site of the polylinker downstream of GAL4-AD of the pGAD10 vector (Clontech), was used for screening according to the manufacturer's instructions. Positive clones were selected, and then cultivated in selective medium depleted of histidine and leucine. The plasmid DNA of the clones was recuperated and introduced by electroporation into the bacterial *Escherichia coli* strain, XL1-blue. The sequencing of the inserts were carried out on a matrix of plasmid DNA purified from a 1.5 ml culture using a mini preparation kit (Bio-Rad, Hercules, Calif., USA). A cDNA library of human thymus cloned in λgt10 (Clontech) was screened by plaque hybridisation to recuperate a cDNA coding for the N-terminal part of the protein.

1.3 Discovery of ICBP-59

The cDNA from four clones selected using the simple hybrid system was sequenced, then analysed employing a digital database (Genbank, EMBL, PDB, Swissprot) to determine the nature of the coded proteins. Two of the clones correspond to ribosomal proteins (hRS12 and hRS4), one to a serine-threonine kinase (STPLK-1), and the fourth to a human protein having theoretical molecular weight of 59 kDa (calculated from the translated sequence) that does not appear in the database.

The cDNA coding for hRS4, hRS12, and ICBP-59, and obtained by EcoRI digestion of positive clones in the pGAD10 vector, were cloned into the EcoRI site of the expression vector pGEX-4T-1 (Pharmacia). The recombinant DNA was then transformed in an adapted mouse *Escherichia coli* strain (BL21). We then used a 500 ml culture of a selected clone once the culture reached a density of 0.5. The overexpression of proteins under study was induced by incubation with IPTG (1 mM) for 2 hours at 37° C. The pGEX-4T-1 vector makes possible the recovery of large quantities of proteins fused to glutathione S-transferase (GST). The GST fusion proteins are then purified using Sepharose beads coupled to glutathione (Pharmacia) followed by overnight cleavage with thrombin (0.05 U/ml) at 4° C. (Pharmacia)

To test the ability of the 59 kDa protein to bind specifically to the ICB1 and/or ICB2 boxes, three tandem copies of ICB2 (ICB2X3, sequences described above) were labelled at the terminal end with 32 P phosphore using the T4 polynucleotide kinase (New England Biolabs) and [$\lambda^{32}$P]ATP (160 mCi/mmol, ICN Irvine, Calif., USA). To examine the specificity of the binding, oligonucleotides containing only one copy of the CCAAT box were synthesized:

ICB1: 5'-AGTCAGGGATTGGCTGGTCTG-';
5'-CAGACCAGCCAATCCCTGACT-3'

ICB2: 5'-AAGCTACGATTGGTTCTTCTG-3';
5'-CAGAAGAACCAATCGTAGCTT-3'.

The ICBP-59 protein (1 μg) was incubated with 1 ng of oligonucleotide and labelled at its terminal end by phosphorous $^{32}$P in 12% glycerol, 12 mM HEPES-NaOH (pH 7.9), 60 mM KCl, 4 mM Tris-HCl (pH 7.9), 100 ng BSA, 0.6 mM DTT, and 100 ng poly(dI/dC) in 20 μl (Inouye et al., 1994). After a 30-minutes incubation at room temperature, the reaction mix was loaded in 6% polyacrylamide gels. In competition experiments, the quantity indicated of non-labelled oligonucleotides were added to the reaction mix 10 minutes before the addition of proteins. To examine the binding properties of ICBP90 with regard to the ICB2 box, we used the same protocol except that labelled oligonucleotide contained only one copy of the CCAAT sequence as described below:

ICB2: 5'-ATAAAGGCAAGCTACGATTGGTTCT-TCTGGACGGAGAC-3' 5'-GTCTCCGTCCAGAAGAAC-CAATCGTAGCTTGCCTTTTAT-3'

Binding specificity was studied using a non-labelled nucleotide containing a GC box of the human topoisomerase IIa promoter:

5'-GCAATTCGAGGGTAAAGGGGCGGGGT-TGAGGCAGATGCCA-3'

5'-TGGCATCTGCCTCAACCCCGCCCCTT-TACCCTCGAATTC-3'.

These gel retardation experiments in acrylamide gels has given us evidence that the new 59 kDa human protein can specifically bind an ICB DNA sequence. We have called this protein ICBP-59 (aminoacid sequence aa 263 to 793 of the sequence SEQ ID NO. 2) (for inverted CCAAT Box Binding Protein of 59 kDa).

EXAMPLE 2

Characterisation of the ICBP90 Protein 2.1. Synthesis of Antibodies

Mouse monoclonal antibodies were synthesized in our laboratory by injection of ICBP-59 protein using traditional methods (Brou et al., 1993); the protein was purified beforehand by a fusion GST system. Two monoclonal antibodies from 1RC1C-10 and 1RC1H-12 were selected for their ability to detect the ICBP-59 endogenous protein; their specificity was demonstrated in both Western blotting and immunocytochemistry experiments. Before use, the antibodies were purified on a DEAE-cellulose column (DE52, Whatmann) from ascites fluid.

2.2 Detection of the Endogenous Protein by Western Blotting

To detect endogenous ICBP-59 protein, we first used 1RC1C-10 in a Western blot (0.4 µg/ml 1RC1C-10 monoclonal antibodies) of nuclear extracts from confluent and proliferating HeLa cells (FIG. 1). COS-1 and HeLa cells were cultivated as previously described (Brou et al., 1993; Gaub et al., 1998; Rochette-Egly et al., 1997). MOLT-4 cells were cultured in 100% air in RPMI supplemented with 10% foetal calf serum. Primary cultures of human pulmonary fibroblasts were prepared and grown in DMEM/F12 as previously described (Kassel et al., 1998). We purchased nuclear extracts of Jurkat cells from Sigma, while we prepared the extracts from MOLT-4 and HL60 as already described in the literature (Lavie et al. 1999). Proliferating HeLa cells and human pulmonary fibroblasts were obtained by depleting their culture media of serum for 30 hours, then reintroducing foetal calf serum to a concentration of 10% (v/v) for 16 hours. Proliferation was arrested when the cells reached 60 to 70% confluence. Cell cultures stopped at confluence (100% confluence) were prepared in the same way, omitting the serum depletion step. For these two types of cells, total cellular extracts were prepared by first harvesting the cells in PBS (phosphate buffered saline), then sonicating them. Immunotransfer experiments on total cell lysates and nuclear extracts involved loading the material on 8% SDS polyacrylamide gels and performing a one-dimensional electrophoresis. The proteins were transferred to nitrocellulose membranes that had been blocked with 10% blocking reagent (Roche Molecular Biochemical, Mannheim, Germany). They were then incubated with 1RC1C-10 purified monoclonal antibodies at a concentration of 0.5 µg/ml. A sheep anti-mouse antibody coupled to alkaline phosphatase (fragments Fab, Roche Molecular Biochemicals) was used at a 1/2500 dilution. The signals were detected using 4-nitro blue tetrazolium 5-bromo-4-chloro-3-indolyl-phosphate chloride as substrate.

These experiments show that the endogenous protein has a molecular weight of approximately 97 kDa. Moreover, we observed that the form of the protein varies according to its tumoural or non-tumoural nature, as well as the state of confluence or proliferation of the cells. For example, in the lanes corresponding to extracts from HeLa cells, there is a major band at 97 kDa; for proliferating HeLa cells, supplementary bands of sizes inferior to 97 kDa appear (lane 2). In confluent human pulmonary fibroblasts, the endogenous protein is not expressed and appears when the cells begin to proliferate (lane 4). These observations suggest that the endogenous protein ICBP90 is a marker of cellular proliferation in normal cells (fibroblasts), while, in tumour cells, it would be a marker at any cellular stage.

The use of monoclonal antibodies in immunoprecipitation experiments on nuclear protein extracts, followed by Western blotting, further puts in evidence the presence of a 97 kDa protein (FIG. 2).

The results obtained from Western blotting, for both nuclear protein extracts and immunoprecipitations, show that the 59 kDa protein isolated by the simple hybrid system constitutes a fragment of the corresponding human endogenous protein, in this case, the C-terminal fragment from residue D263. It was, therefore, necessary for us to undertake a new screening of the cDNA library.

2.3. Multiple Human Tissues RNA Dot Blot Analysis

In order to choose a library providing us with the best possible chance to isolate the complete protein, we wanted to identify a human tissue expressing the corresponding messenger RNA (mRNA) With a 32P labelled cDNA probe covering part of the ICBP59 sequence, we tested the mRNA expression of interest in 50 different human tissues against a RNA Dot Blot. Briefly, a 678 base pair probe corresponding to the ICBP90 amino acids sequence 269 to 500 was synthesized by PCR using Taq polymerase (Sigma, St Louis, Mo., USA). The probe labelled by random priming using dCTP—α 32P was purified on Sephadex G50 columns (Pharmacie, Uppsala, Sweden).

A multiple organ RNA Dot Blot containing poly(A); RNA from 50 different human tissues was hybridised for 20 hours under strong stringency conditions in an ExpressHyb environment (Clontech) at 68° C. with a 32P labelled probe. High stringency washing was completed in 0.1×SSC, 0.1% SDS at 68° C. (De Vries et al., 1996).

The results obtained (FIG. 5) show that tissues expressing most strongly the ICBP-59 protein mRNA are adult and foetal thymus, as well as adult bone marrow and foetal liver. Therefore, to isolate the whole protein, we choose an adult thymus cDNA librairy.

2.4. Librairy Screening and ICBP90 Cloning

The bank screening permitted us to obtain several clones of about 4000 base pairs (bp) containing a 2379 bp open reading frame (FIG. 6). This sequence codes for a 793 amino acid protein (FIG. 7), which theoretical molecular weight (calculated from the translated sequence) is 89.758 kDa. We called this protein ICBP90 (for Inverted CCAAT Box Binding Protein of 90 kDa) by analogy to the initial 59 kDa protein name.

The ICBP90 cDNA (2379 bp) was synthesized by PCR using Deep Vent DNA polymerase (New England Biolabs, Beverly, Mass., USA) and oligonucleotides used during this PCR reaction were near the EcoRI site. The product of the reaction was thereafter sub-cloned in a pGEX-4T-1 vector (Pharmacie) for the GST fusion protein expression in BL21. The over expression was induced by IPTG (1 mM) for 4 h at 25° C. The ICBP90 protein was then purified.

2.5. Immunocytochemistry and Immunohistochemistry

The direct observation of the ICBP90 protein on cells and tissues was also carried out.

COS-1 cells were transfected as describes previously (Brou et al., 1993; Gaub et al., 1998) with the pSG5 vector (Stratagene, La Jolla, Calif.) in which the ICBP90 cDNA (2379 bp) was sub-cloned in the EcoRI restriction site. The cDNA was synthesized by polymerisation chain reaction (PCR) using Deep Vent polymerase (New England Biolabs) and the oligonucleotides flanking the EcoRI restriction site. Plasmidic construction was verified by sequencing. The immunolabelling of the transfected lleLas and COS-1 cells was achieved as described previously (Brou et al., 1993) with 1RC1C-10 and 1 RC1H-12 monoclonal antibodies, respectively. An indirect labelling with ICBP90 immunoperoxidase and IIα topoisomerase was achieved as described previously (Rio et al., 1987, Devys et al., 1993). Human appendices were embedded in paraffin and fixed in 10% buffered formalin (Sigma). Serial sections (3 gm) were incubated overnight at room temperature with 1RC1C-10 antibody and with IIα anti-topoisomerase antibody (Neo-Markers, Union City, Calif., USA). Antibodies bound in a specific manner are visualized through a complex using streptavidine biotin (LAB/LSAB method, Dako LSAB2 System kit; DAKO, Carpinteria, Calif., USA).

In immunocytochemistry the 1RC1C-10 antibody labels the HeLa cells nucleus whereas the nucleolus and the whole cytoplasm are not labelled (FIG. 3). In immunohistochemistry, paraffin-embedded human appendix sections show labelling essentially localized in cellular proliferation zones (FIG. 4). Indeed, the labelled cells were located in the glandular crypts (CG) as well as in the germinative zones (Ger). An identical labelling is obtained when using an IIα anti-topoisomerase antibody, an enzyme essentially expressed in proliferating cells (results non illustrated).

2.6. BLAST Research and Domain Prediction

Studies about on-line BLAST have been carried out based on information from the National Centre for Biotechnology Information at the National Institute of Health (Bethesda, Md., USA). SCANPROSITE and PROFILESCANS were used for protein analysis (Infobiogen, Villejuif, France).

ICBP90 includes a "ubiquitin like" domain in its first 80 amino acids, two sites of potential nuclear localizations in its C terminal and two zinc finger-like domains, one of which could be implicated in the DNA linkage and the other in protein—protein interactions. Several potential phosphorylation sites by protein kinase C, the casein kinase II, as well as by a tyrosine kinase, were also present.

ICBP90 production and purification using the GST fusion system (same procedure as for ICBP-59) permitted to finally test the complete protein ability to link the ICB type DNA sequences. Its behaviour is identical from top to bottom to that observed for ICBP-59.

Finally, we isolated a new human protein that we called ICBP90 for the reasons evoked above. Its theoretical molecular weight is 89.758 kDa and its apparent molecular weight on acrylamide gel is 97 kDa. This protein is not only localized exclusively in human cell nuclei, but it also presents the ability to bind specifically DNA sequences, in this case CCAAT type sequences. For these reasons, we think that ICBP90 has the possibility to modulate the expression of genes which promoter is provided with CCAAT boxes, possibly in reversed position (ICB). The gene of the human topoisomerase IIα we are especially interested in, and which includes five ICB sequences in its promoter, seems to be one of ICBP90 privileged targets.

These experiences allowed to bring to light the 1RC1C-10 antibody remarkable features, which only labels proliferating cells in the case of non cancerous cells; it labels both proliferating and quiescent cancerous cells; it is usable with 4 different techniques (Western blotting, Immunocytochemistry, immunohistology, immunoprecipitation); it has a very good affinity and allow for the use of $\frac{1}{150,000}$ dilution in immunohistochemistry (13 ng/ml); finally, its use generates nearly no background noise.

Future applications of 1RC1C-10 are primarily for diagnostic and basic research. For anatomo-pathologic diagnostics for instance, it would be quite possible to assess the proliferative state of a given cancerous tissue. Regarding basic research, investigations are in progress in our laboratory in order to determine the exact contribution of ICBP90 to proliferation mechanisms in normal and cancerous cells. However, the use of antibodies will be required to study ICBP90 expression as a function of the cellular cycle, of its precise nuclear localization and of its interaction with other cellular proteins.

At the moment we haven't study the expression of ICBP90 with regards to cellular cycle. Nevertheless, in the case where cancerous cell lineages are confluent or when they are not proliferating, we can detect significant differences of ICBP90 expression (FIG. 1) at least with regard to the 97 kDa form. On the other hand, in the non-cancerous confluent cells (human bronchial smooth muscular cells) the ICBP90 expression is hard to detect (results not illustrated). This was confirmed with histological sections where no quiescent cells were labelled by the antibody. It is therefore possible that ICBP90 is expressed whatever the cellular cycle phase in cancerous cells whereas its expression would vary according to each phase in non-cancerous cells. Therefore, this makes the use of the antibody extremely interesting, as, contrary to other cellular proliferation label such as Ki-67, topoisomerase IIα, cycline E and cycline B1, we would have at our disposition a label for cancerous tissue proliferating cells that would not depend on the cellular cycle phase. Indeed, the end of the S phase is characterized by a very weak Ki-67 expression, cycline E labels cells at the end of phase G1 up to the middle of phase S, and cycline B1 labels cells in phase G2/M (for a review, see Darzynkiewicz et al., 1994). Moreover, it has been shown that PCNA (Proliferating Cell Nuclear Antigen) overestimates the number of proliferating cells in some types of tissues (Roskell and Biddolph, 1999).

ICBP90 plays an important role in cellular proliferation by regulating the expression of genes such as those for topoisomerase IIα. Different strategies aiming at blocking the action of this protein must allow modifying cellular proliferation. Anyway, the uses of the 1RC1C-10 antibody as well as of peptides mimicking the ADN/ICBP90 interaction without generating subsequent physiological effect constitute an interesting possibility. The design of its peptides would be directly inspired from the ICBP90 protein sequence we described. A truncated form corresponding to ICBP59 could be one of the first candidates, for instance.

The simple blockage of ICBP90 expression in order to completely eliminate its influence on genes and, by extension, on cellular proliferation can be considered; it could be carried out either by a classic approach such as obtaining inhibitors of the protein, or by a more modern approach corresponding to the interference technique with-double strand RNA (RNA interference or RNAi) as describes recently by Kennerdell & Carthew (1998).

EXAMPLE 3

Isolation and Characterization of Gene ICBP90

3.1. Material and Methods 3.1.1. Construction and Screening of a Human Placental Genomic Library After partial digestion with MboI enzyme, the placental genomic DNA was split up according to size on a 10 to 40% sucrose gradient. Fifteen kb DNA Fragments were ligated in a λGEM 12 vector previously digested with BamHI (Promega, Madison WI, USA). After packaging, phage λ particles were assayed on TAP 90 cells. The genomic library contains $3.10^6$ plaque-forming units (pfu). $10^6$ clones were spread out for analysis. A 620 bp probe corresponding to a 5' terminal extremity of the ICBP90 cDNA used for the screening was labelled with α32P-dCTP by a random priming method (Sambrook et al., 1989). The labelled probe is used according to a classic on plaque hybridisation protocol to screen the genomic library (Sambrook et al., 1989). Hybridisation was achieved at 68° C. in 5×SSC (15 mM NaCl, 1.5 mM sodium citrate pH 7.0), 5× Denhardt solution, 100 μg/ml of salmon sperm DNA, and 0.1% SDS, followed by 30 minutes washing in 2×SSC, 0.1% SDS at room temperature.

Two screening steps were completed to purify a positive clone. The positive clone was then digested with NotI enzyme and two fragments of 6 and 10 kb were sub-cloned in pBluescript SK$^+$ vector (Stratagene, La Jolla Calif., USA) following a standard protocol (Sambrook et al., 1989).

3.1.2. Librairy Screening of Human Thymus cDNA

A bank λGT10 of human thymus cDNA 5' end (Clontech, Palo Alto, Calif., USA) has been screened by on plaque hybridisation using the 679 bp cDNA probe synthesized as in the paragraph concerning Northern Blotting Analysis. Signals were detected using 4-nitro-blue tetrazolium chloride and 5-bromo-4-chloro-3-indolyl-phosphate as substratum.

3.1.3. Polymerisation Chain Reaction (PCR) on Placental Genomic DNA

Placental genomic DNA was prepared according to a conventional method (Sambrook et al., 1989). For the 5' region of gene ICBP90, inventors used the PCR Advantage©GC genomic kit from Clontech which is adapted to the genomic DNA regions rich in GC. To cover the 3'-flanking regions, Taq polymerase (Sigma, St Louis, Mo., USA) and its corresponding buffer was used. Reactions were achieved according to the manufacturer's instructions while using 250 ng of placental genomic DNA as matrix in a final volume of 50 μl. In order to obtain the 19 kb and 8.7 kb long intron amplification, the PCR Expand™ 20 kb$^{plus}$ system (Roche Diagnostics, Mannheim, Germany) was used.

The reaction was completed in 100 μl using 125 ng of placental genomic DNA by reaction.

3.1.4. Plasmidic Constructions and CAT Assays

A set of various fragments was obtained by PCR in the 5' flanking region of gene ICBP90 using 20 nucleotide primers in order to obtain the construction described in FIG. 10. These contain a BamHl restriction site, and a human placental genomic DNA was used as primer. The PCR products were digested and sub-classified upstream from the chloramphenicol acetyl transferase (CAT) reporter gene of a vector containing the thymidine kinase minimal promoter (pBl-CAT2). Plasmidic constructions were verified by sequencing. COS-1 cells were cultivated in a Dulbecco milieu modified by Eagle (DMEM) supplemented with 5% foetal calf serum. After the spreading, the cells were transferred with the various plasmidic constructions (5 μg) using the co-precipitation technique with calcium phosphate (Banerji et al., 1981). Analyses of CAT expression were then carried out as describes elsewhere (Goetz et al., 1996)

3.1.5. Chromosomal Localization of Gene ICBP90

Some metaphasic chromosomes were prepared from human peripheral blood leukocytes according to standard protocols (Haddad et al., 1988). Briefly, a 10 kb probe corresponding to a 5' terminal fragment of the 16 kb clone isolated from the placental genomic DNA screening library, was labelled with biotine-16-dUTP (Roche Diagnostics) by "nick-translation". The probe was then precipitated with an excess (50×) of Cot-1 human DNA (Life Technologies, Rockville Md.), resuspended in 50% formamide, 1×SSC, pre-hybridised for 2 hours at 37° C. then hybridised overnight at 37° C. The detection was carried out using avidin-FITC (Vector Laboratories, Burlingam Calif.). Chromosomes were counter-stained with 4'-6-diamino-2-phénylindole (Sigma).

3.1.6. Northern and Western Blotting Analysis

A Northern Blotting membrane containing 2 μg of polyA+ RNA by line, coming from 7 different human cancerous cell lines (Clontech) was pre-hybridised in Express Hyb (Clontech), then hybridised with the specific ICBP90 probe in Express Hyb at 68° C. for two hours. The double-strand probe labelled with digoxigenin was prepared from PCR amplification of a 676 bp fragment from ICBP90 cDNA (nucleotides 806 to 1485; Genbank accession number AF 129507) according to the manufacturer's instructions (Roche Diagnostics).

After purification through a Micro Bio-Spin 30 chromatography column (Bio Rad, Hercules, Calif.), the specific ICBP90 probe (5 ng/ml) was heated at 95° C. for 15 minutes then cooled on ice before addition of the hybridisation solution. Washing after hybridisation were carried out twice in 2×SSC, 0.1% SD (30 minutes per wash at room temperature), then twice in SSC 0.1×, 0.1% SD (30 min per wash at 68° C.). The membrane was treated with solution A (0.1 M malic acid, 0.15 M NaCl at pH 7.5) then blocked by incubation with 1% blocking agent (Roche Diagnostics) in buffer A for 30 min at room temperature.

An antibody conjugated to alcaline-phosphatase directed against the digoxigenin (Fab fragment, Roche Diagnostics) was added (150 mU/ml) then incubated for 30 min at room temperature. The membrane was then washed twice with solution A, then balanced in 0.1 M tris-HCl, 0.1 M NaCl, pH 9.5. For the detection by chemiluminescence, the inventors used agent disodium 3-(4-methoxyspiro{1,2-dioetane-3,2'-(5'-chloro)tricyclo-[3,3.1.$1^{3,7}$]decan}-4-yl) phenyl phosphates (Roche Diagnostics) according to the manufacturer's instructions. mRNA strips were quantified using the NIH software Image 1.62 and expressed as a percentage of the most abundant mRNA strip (e.g. the 5.1 kb strip of HL-60 cells).

Western Blotting analysis was carried out as describes elsewhere (Hopfner et al., 2000). Signals were detected using 4-nitro-blue tetrazolium chloride and 5-bromo-4-chloro-3-indolyl phosphate as substrate.

3.1.7. Local Base Alignment Research Tools, Primer Transcription and PolyA Signal Sites Predictions Local base alignment research tools was completed via the National Biotechnology Information Center at the National Institute of Health (Bethesda, Md., USA). The transcription factor library screening with Mat Inspector software, the primer transcription site predictions (TSS)

with Neural Network, as well as the polyA signal prediction, were all carried out at Baylor College of Medicine (Reese et al., 1996).

3.2. Results 3.2.1. Isolation and Characterization of Gene ICBP90

A DNA complementary library of human placenta cloned within the lambda GEM 12 phage was screen using a DNA probe. The screening lead to the purification of a single positive clone with a 16 kb insert. The sequence analysis permitted to determine that it contained a 10 kb intronic sequence containing 3 exons (called B, C, and D in FIG. 9A). All others screenings, namely including those completed with PCR on BAC (Bacterial Artificial Chromosome) or YAC (Yeast Artificial Chromosome) banks, failed to yield other positive clones. Therefore, we decided to determine the remainder of the gene organization directly by PCR on human placenta genomic DNA. The biggest difficulty was to get the 5' end of the 19 kb intron. Primers were so chosen in exon A (sense primer) and in the 5' end of the 16 kb clone (anti-sense primer). The exon E and the 8.7 kb intron were amplified using a sense primer in exon D and anti-sense primer in exon F. Finally, the complete sequence of exon F up to the poly-adenylation signal was determined using a sense primer chosen at the beginning of exon F and the anti-sense primer in the 3' end of an EST (reference in GenBank No. AW297533) homologous to Gene ICBP90 sequence. The complete sequence of gene ICBP90 shows that it is made of 6 coding exons which size varies from 100 bp to 3453 bp. Most exon/intron junctions match consensus sequences for splicing acceptor and donor sites. A polyadenylation (AATAAA) consensus sequence was found in the 3' region, e.g. 1152 nucleotides after the stopping codon in FIG. 9A.

3.2.2 The 5' Region of Gene 11OEP90

The complementary DNA screening library of human thymus cloned in lambda gt 10 phage lead to obtaining two cDNA populations distinguishing one another from their 5' region, precisely 10 base pairs upstream from the primer codon, i.e. in the non-translated 5' region. These two cDNA populations predict the existence of two alternative exons in 5' called exon I and II (FIG. 9A). We observed that exons I and II are linked to an alternative internal splicing site of exon A. Moreover, in a database, we found an EST (reference in GenBank No. AI084125) corresponding to nucleotides 1290 to 1356 (FIG. 9B). The positions of these two exons and of the EST inside the locus were determined by PCR. For that, we used primers corresponding to the first 18 nucleotides of each exon and an anti-sense primer selected from the first exon translated (exon A). This strategy permitted us to rebuild the 5' region as represented in FIGS. 9A and 9B, with exon I corresponding to nucleotides 1 to 134 and exon II corresponding to nucleotides 676 to 725. The EST sequence (AI084125) is adjacent to exon A internal splicing site. We haven't determine yet with precision the beginning of exons I, II, and A since their sequences have been deducted from cDNA bank screenings (FIG. 9A).

Four CC boxes (GC1 to GC4) have been found in the 5' region (FIG. 9B). These boxes represent the potential sites of linkage for the Sp1 transcription factor, but only one box (GC3) corresponds to a consensus sequence, e.g. GGGGCGGGG. Besides two CCAAT boxes (CB1 and CB2) were found. Predictive analyses of sequences suggest that two promoter regions exist in the 5' region, e.g. before the initiation codon (ATG). Two potential transcription initiation sites have been predicted in positions 571 and 827. The first follows the linkage consensus sequence of Sp1 and the second follows the GC1 box (between exons I & II, and exons II & A, respectively). In order to determine if these two regions are functional as promoter region, several plasmidic constructions containing a reporter gene (the Chloramphenicol Acetyl Transferase gene; CAT) downstream from the various potential promoters regions were prepared. COS cells were transfected with these plasmidic constructions. FIG. 10 shows the results obtained corresponding to a percentage of increased basal activity. The maximal activity was obtained with the plasmidic construction containing 1114 bp upstream from the translation initiation site, with a 236.7% increase of basal promoter activity (thymidine kinase gene minimal promoter). The plasmidic construction containing 642 bp upstream from ATG lead to a 115.6% increase whereas plasmidic construction containing the sequence solely between exon I and II showed a comparatively weak activity with only a 22.8% increase (FIG. 10). These results suggest the existence of a promoter region between exons II and A.

3.2.3. Chromosomal Localization of Gene ICBP90

The chromosomal localization of gene ICBP90 was completed by fluorescence in situ hybridisation (FISH). Gene ICBP90 is localized on chromosome 19p13.3 in a telomeric region. A research carried out at Genbank showed that a 6 Mb region in the chromosomal strip 19p 13.3 of a chromosome 19 (hybrid human/hamster 5HL2 B) specific cosmid bank contains 147 nucleotides coding for ICBP90 amino acids 746 to 793. This sequence has been localized between the STS (sequence tagged site) markers D 19S883 and D 19S325.

3.2.4 ICBP90 Expression in Various Cellular Lineages

ICBP90 participates in the regulation of the gene TopIIα expression (Hopfner et al., 2000). As TopIIα is expressed 3rd differential manner in various tumours and cellular lineages, ICBP90 itself is susceptible to have a complex regulation in term of activity and genic expression.

In a first step towards understanding the mechanisms regulating gene ICBP90 expression, ICBP90 mRNA was analysed in various cellular lineages. ICBP90 mRNA was studied in the HL60 cellular lineage derived from promyelocytic leukaemia (lineage 1), Hela S3 cells (lineage 2), MOLT-4 lymphoblastic leukaemia cells, Raji Burkitt lymphoma cells (lineage 5), SW 480 colorectal adenocarcinoma (lineage 6), A549 lung carcinoma cells (lineage 7) (FIG. 11A).

Two 4.3 and 5.1 kb bands of mRNA are observed. The relative amounts of mRNA in the bands vary according to the cell type. The histogram in FIG. 11A shows the levels of mRNA in the bands of each of the cell lines, expressed in percentage of the maximum amount of 5.1 kb bands of mRNA observed in the HL-60 cells (line 1, FIG. 11A). In the MOLT-4 cells, only the 4.3 kb band of mRNA is observed, while in the cells from promyelocytic leukaemia the 5.1 kb band is predominant. In the Raji cells of Burkitt's lymphoma, only the 5.1 kb band is detected. Approximately equal amounts of the two types of mRNA are observed in the other cell lines, that is, the Hela, K562, A549, SW580 cells. For the HL-60 cells, nevertheless, the 5.1 kb mRNA is more strongly expressed than the 4.3 kb mRNA. Other analyses have been undertaken on the Hela cells to confirm that the 2 transcripts originate from the transcription of the ICBP90 gene. A cDNA probe of 626 bp labelled with digoxigenin localized immediately upstream of the poly A signal (that is, the exon F) and used as probe for Northern Blotting experiments, has produced the same results, that is, the appearance of two 4.3 kb and 5.1 kb bands of mRNA. This result confirms that the two forms of mRNA are generated from a single gene.

The inventors have also studied the expression of the ICBP90 protein in order to determine if these two isoforms of mRNA are likely to code for two different proteins.

FIG. 11B shows the expression profile of ICBP90 in protein extracts of MOLT-4 and Hela cells. While a single band of 97 kDa is observed in the MOLT-4 cells, in the Hela cells, beside the 97-kDa band that is doubled, several other bands with a lower molecular weight are observed. These results suggest that in the MOLT-4 cells, an mRNA codes for a single form of ICBP90. Conversely, in the Hela cells, the two mRNA are likely to lead to the production of different isoforms of ICBP90.

3.3 Comments

The ICBP90 gene is spread over approximately 35.8 kb. Six translated exons and two untranslated exons, and then, seven introns have been identified by the inventors. The two zinc-finger domains of ICBP90 are coded by the same exon (exon F) in contrast to the receptor gene for human estrogens in which each of the presumed zinc fingers of the DNA binding domain of the receptor are coded separately (Ponglikitmongkol et al. (1988)). The "ubiquitin-like" domain of ICBP90 is coded by exons A and B while the "leucine zipper" is coded by exon B. Interestingly, only exon F is likely to code for a functional protein because it codes for two nuclear localization signals, the zinc-finger domains and several presumed sites of phosphorylation. Two large 8.7 kb and 19 kb introns have been found.

The ICBP90 gene has been localized in the chromosome region 19p13.3. Several other genes have been localized in this region, for example the Nuclear Factor I/C (also a CCAAT binding transcription factor) (Qain et al. (1995)). Interestingly, an atypical translocation t(7;19) in the acute myelomonocytic leukaemia, involving a fragile site at the 19p13.3 locus has been described (Sherer et al. (1991)). Also, it has been suggested that the genes involved in the development of pancreatic carcinomas are localized at 19p13.3 and 19q13.1–13.2 (Hoglund et al. (1998)). Rearrangements of the 14q32.3 and 19p13.3 bands with a preferential deletion of the short arm of chromosome 1 form non-random chromosome alterations in multiple myeloma and leukaemia of cells of the plasma (Taniwaki et al. (1996)). Other genes have been localized in this region; they include a gene involved in adenocarcinoma of the Peutz-Jeghers syndrome (Gruba et al. (1998)). Also, it has been suggested that the presumed tumour suppressor gene for malignant adenoma is localized on D19S216 at the 19p13.3 chromosome band that plays an important role in tumourigenesis of malignant adenoma (Lee et al. (1998)).

The analysis of the sequence of the 5' region of the ICBP90 gene has revealed the existence of several untranslated exons with a promoter region between exons II and A and probably a second weaker promoter localized between exons I and II. The promoter region between exons II and A is a promoter without TATA sequence suggesting that the ICBP90 gene may be a housekeeping gene at least when this promoter is involved. In this sense, it strongly resembles promoter regions of the genes ATFα (Goetz et al., 1996), CRE-BP1/ATF2 (Nagase et al., 1990) and TopIIα (Hochhauser et al., 1992) which do not contain canonical TATA boxes but several SP-1 binding sites.

The GC and/or CCAAT boxes are likely to be involved in the regulation of the expression of the ICBP90 gene via transcription factors SP-1 and the CCAAT binding proteins. Furthermore, given that the ICBP90 protein is a CCAAT binding protein, ICBP90 is also likely to regulate its own expression.

A data library of transcription factors has been screened with the aid of the Mat Inspector computer program from the Baylor College of Medicine and numerous binding sites of transcription factors have been identified in the sequence preceding the ATG codon (FIG. 9B). Among these binding sites for the transcription factors it is interesting to note binding sites of the AP-2 transcription factor regulated during the development and which controls the DR-nm23 gene expression (Martinez et al. (1997)), the binding sites of the "zinc-finger" myeloid protein MZF 1 which is involved in the regulation of hematopoiesis (Hromas et al. (1996)).

The Northern Blotting analysis has demonstrated that two populations of mRNA exist, 4.3 kb and 5.1 kb. Interestingly, each population presents a cellular specificity. For example, the lymphoblast cells MOLT-4 only express the 4.3 kb mRNA, while in the Raji cells of Burkitt's lymphoma (mature B lymphocytes), only the 5.1 kb transcript is observed. The HL-60 cells express more 5.1 kb mRNA then 4.3 kb mRNA. The HL-60 cells and the Raji cells of Burkitt's lymphoma are more differentiated than the MOLT-4 cells suggesting that the levels of expression of the 5.1 kb transcript relative to that of 4.3 kb may be directly correlated with the state of differentiation of the cells.

Interestingly, an expressed sequence tag (EST, Expressed Sequence Tag) corresponding to the 5' sequence of the exon A has been identified from anaplastic oligodendroglioma (Genbank Accession No. AI 084 125) while an EST corresponding to the inclusion of exon II has been isolated from a mixture of tumours with germinal cells (Genbank Accession No. AI 968 662). The results of the inventors therefore suggest that the regulation of the ICBP90 transcripts is comparable to that which happens with the oestrogen receptor. In fact, six different transcripts coding a common protein, but differing in the untranslated 5' region because of an alternative splicing of upstream exons, have been reported (Flouriot et al., 1998 and Grandien, 1996).

The Western Blotting analysis shows a major band at 97 kDa in the MOLT-4 cells while several bands are observed in the Hela cells (FIG. 11B). This data is in agreement with the existence of several ICBP90 mRNA and/or isoforms of the ICBP90 protein for which the level of expression may be controlled in a cell-specific manner.

Two protein isoforms for the oestrogen receptor have been described (Griffin et al., 1999) which differ from each other by the 41 N-terminal amino acids. The 97 kDa double band observed from the Hela cells (FIG. 11B) is therefore likely to represent two isoforms differing by their N-terminal end. To do this, the exon A coding for 47 amino acids is spliced outside the reading frame, and consequently, the protein-coding region begins with exon B. Nevertheless, it is also possible that there are other exons likely to be transcribed in other tissues.

Also, the 8.7 kb intron (that is, between exon D and E) is likely to contain a promoter region which may lead to ICBP90 isoforms with lower molecular weight than those observed in the Hela cells in proliferation (FIG. 11B). Interestingly, the tissue specificity of the different mRNA of the oestrogen receptor is determined by different promoters for which the activity appears to be altered in the cell lines of breast cancer (Flouriot et al., 1998).

All these results suggest that the ICBP90 gene and the ICBP90 protein present characteristics common with members of the family of the receptor for retinoic acid, steroids, thyroid hormones where it concerns gene and protein structures.

In fact, the inventors have demonstrated experimentally, by using the double-hybrid technique, the existence of interactions between the ICBP90 protein and TIP60 (Tat Interactive Protein, 60 kDa). The TIP60 protein has very recently been described as being a coactivator of the nuclear receptor, especially the receptor for the androgens (Brady M E et al., 1999).

Because of this, ICBP90 is capable of playing the role of a nuclear receptor on which an endogenous ligand is bound. Therefore, it is also within the scope of the present invention to use the ICBP90 polypeptide of the invention to isolate, screen, and identify the endogenous ligand. It is also within the scope of the invention to use the ICB90 polypeptide of the invention to isolate, screen identify natural or synthetic, biological or chemical, agonist or antagonist molecules of this natural ligand.

REFERENCES

Austin et al. (1993), Biochem. Biophys. Acta, 1172, 283–291
Banerji, J. et al. (1981), Cell, 27: 299–308.
Barany, F. (1991), Proc. Natl. Acad. Sci. USA, 88, 189–193.
Boritzki, T. J. et al. (1988), Biochem. Pharmacol., 37, 4063–4068.
Brady, M. E. et al. (1999), J. Biol. Chem., 274: 17599–17604.
Brandt, T. L. et al. (1997), J. Biol. Chem., 272, 6278–6284.
Brou, C. et al. (1993), EMBO J., 12, 489–499.
Buckholz, R. G. (1993), Curr. Op. Biotechnology, 4, 538–542.
Burg, J. L. et al. (1996), Mol. and Cell. Probes, 10, 257–271.
Chu, B. C. F. et al. (1986), Nucleic Acids Res., 14, 5591–5603.
Chung, T. D. Y. et al. (1989), Proc. Natl. Acad. Sci. USA, 86, 9431–9435.
Darzynkiewicz et al. (1994), Methods in Cell Biology, 41, 421–435.
Deffie, A. M et al. (1989), Cancer Res., 49, 58–62.
DeVries, L. et al. (1995), Proc. Natl. Acad. Sci. USA, 92, 11916–11920.
Devys et al. (1993), Nature Genet., 4, 335–340.
Drake, F. H. et al., Biochemistry, 28, 8154–8160.
Duck, P. et al. (1990), Biotechniques, 9, 142–147.
Edwards, C. P. and Aruffo, A. (1993), Curr. Op. Biotechnology, 4, 558–563.
Erlich, H. A. (1989), New York: Stockton Press.
Flouriot et al. (1998), Mol. Endocrinol., 12:1239–254.
Fry, A. M. et al. (1991), Cancer Res., 51, 6592–6595.
Furth et al. (1992), Anal. Biochem., 205: 365.
Gaub, M. P. et al. (1998). J. Histochem. Cytochem., 46, 1103–1111.
Goetz, J. et al. (1996), J. Biol. Chem., 271: 29589–29598.
Goswami, P. C. et al. (1996), Mol. Cell. Biol., 16, 1500–1508.
Grandien (1996), Mol. Cell. Endocrinol., 116: 207–212.
Griffin et al. (1999), Mol. Endocrinol., 13: 1571–1587.
Gruba et al. (1998), Cancer Res., 58: 5267–5270.
Guatelli, J. C. et al. (1990), Proc. Natl. Acad. Sci. USA, 87, 1874–1878.
Guinee, D. G. et al. (1996), Cancer, 78, 729–735.
Haddad et al. (1988), Human Genet. 103: 619–625.
Heck, M. M. et al. (1988), Proc. Natl. Acad. Sci. USA, 85, 1086–1090.
Herzog, C. E. and Zwelling, L. A. (1997), Biochem. Biophys. Res. Commun., 232, 608–612.
Hochhauser, D. et al. (1992), J. Biol. Chem., 267, 18961–18965.
Hoglund et al. (1998), Genes Chromosomes Cancer 21:8–16.
Hopfner et al. (2000), Cancer Res., 60:121–128.
Hromas et al. (1996), Curr. Top. Microbiol. Chem., 211: 159–164.
Innis, M. A. et al. (1990), Academic Press.
Inouye, C. et al. (1994), DNA Cell Biol., 13, 731–742.
Isaacs, R. J. et al. Biochem. Biophys. Acta, 1400, 121–137.
Isaacs, R. J. et al. (1996), J. Biol. Chem., 271, 16741–16747.
Jenkins, J. R. et al. (1992), Nucleic Acids Res., 20, 5587–5592.
Kassel, O. et al. (1998), Mol. Pharmacol., 54, 1073–1079.
Kennerdell, J. R. and Carthew, R. W. (1998), Cell, 95, 1017–1026.
Kievitis, T. et al. (1975), J. Virol. Methods, 35, 273–286.
Kohler, G. et al. (1975), Nature, 256 (5517), 495–497.
Kubo, T. et al., (1995), Cancer Res., 55, 3860–3864.
Kwoh, D. Y. et al., (1989), Proc. Natl. Acad. Sci. USA, 86, 1173–1177.
Landegren, U. et al. (1988), Science, 241, 1077–1080.
Lavie, J. et al. (1999), J. Biol. Chem., 274, 2308–2314.
Lee et al. (1998), Cancer Res., 58: 1140–1143.
Lim, K. et al. (1998), Biochem. Mol. Biol. Int., 46, 35–42.
Lizardi, P. M. et al. (1988), Bio/technology, 6, 1197–1202.
Lucknow, V. A. (1993), Curr. Op. Biotechnology, 4, 564–572.
Martinez, et al. (1997), Cancer Res., 57: 1180–1187.
Matthews, J. A. et al. (1988), Anal. Biochem., 169:1–25.
Miele, E. A. et al. (1983), J. Mol. Biol., 171, 281–295.
Nagase et al. (1990), J. Biol. Chem., 265:17300–17305.
Nitiss, J. L. (1998), Biochem. Biophys. Acta, 1400, 63–81.
Olins, P. O. and Lee, S. C. (1993), Curr. Op. Biotechnology, 4, 520–525.
Pommier, Y. et al. (1994), Cancer Invest., 12, 530–542.
Ponglikitmongkoi et al. (1988), EMBO J. 7:3385–3388.
R10, M. C. et al. (1987), Proc. Natl. Acad. Sci. USA, 84, 9243–9247.
Qian et al. (1995), Genomics, 28:66–73.
Reese et al. (1996), Large Scale Sequencing Specific Neural Networks for Promoter and Splice Recognition. Biocomputing: Proceedings of the 1995 Pacific Symposium. Edited by Lawrence Hunter and Terri E. Wood Scientific Singapore, 1996, Jan. 27, 1996.
Rochette-Egly, C. et al. (1997), Cell, 90, 97–107.
Roskell, D. E. and Biddolph, S. C. (1999), Eur. J. Med. Res. 26, 105–106.
Rolfs, A. et al. (1991), Berlin: Springer-Verlag.
Sambrook, J. et al. (1989), Molecular Cloning: A Laboratory Manual, Sec. Ed. Cold Spring Harbor Lab., Cold Spring Harbor, N.Y.
Sandri, M. I. et al. (1996), Nucleic Acids Res., 24, 4464–4470.
Segev, D. (1992), Kessler C. Springer Verlag, Berlin, New York, 197–205.
Sherer et al. (1991), Cancer Genet. Cytogenet., 57: 169–173.
Stone, B. B. et al. (1996) Mol. and Cell. Probes, 10:359–370.
Tang et al. (1992), Nature, 356:152.
Taniwaki et al. (1996), Leuk. Lymphoma, 21:25–30.
Tsai-plugfelder, M. et al. (1988), Proc. Natl. Acad. Sci. USA, 85, 7177–7181.
Walker, G. T. et al. (1992), Nucleic Acids Res., 20:1691–1696.
Wang, J. C. (1996), Ann. Rev. Biochem., 65, 635–692.
Wang, M. M. and Reed, R. R. (1993), Nature (London), 364, 121–126.
Yamazaki et al. (1996), Acta Oncol., 35, 417–423.

The invention claimed is:

1. An isolated polypeptide comprising the amino acid sequence SEQ ID NO 2.

2. An isolated polypeptide consisting of a fragment of the amino acid sequence SEQ ID NO 2, wherein said fragment comprises amino acids 263–793 of the amino acid sequence SEQ ID NO:2.

* * * * *

SEQUENCE LISTING

<160> NUMBER OF SEQ ID NOS: 24

<210> SEQ ID NO 1
<211> LENGTH: 2382
<212> TYPE: DNA
<213> ORGANISM: Homo sapiens
<220> FEATURE:
<221> NAME/KEY: CDS
<222> LOCATION: (1)..(2379)

<400> SEQUENCE: 1

| | | | | | | | | | | | | | | | | |
|---|---|---|---|---|---|---|---|---|---|---|---|---|---|---|---|---|
| atg | tgg | atc | cag | gtt | cgg | acc | atg | gat | ggg | agg | cag | acc | cac | acg | gtg | 48 |
| Met | Trp | Ile | Gln | Val | Arg | Thr | Met | Asp | Gly | Arg | Gln | Thr | His | Thr | Val | |
| 1 | | | | 5 | | | | | 10 | | | | | 15 | | |
| gac | tcg | ctg | tcc | agg | ctg | acc | aag | gtg | gag | gag | ctg | agg | cgg | aag | atc | 96 |
| Asp | Ser | Leu | Ser | Arg | Leu | Thr | Lys | Val | Glu | Glu | Leu | Arg | Arg | Lys | Ile | |
| | | | 20 | | | | | 25 | | | | | 30 | | | |
| cag | gag | ctg | ttc | cac | gtg | gag | cca | ggc | ctg | cag | agg | ctg | ttc | tac | agg | 144 |
| Gln | Glu | Leu | Phe | His | Val | Glu | Pro | Gly | Leu | Gln | Arg | Leu | Phe | Tyr | Arg | |
| | | 35 | | | | | 40 | | | | | 45 | | | | |
| ggc | aaa | cag | atg | gag | gac | ggc | cat | acc | ctc | ttc | gac | tac | gag | gtc | cgc | 192 |
| Gly | Lys | Gln | Met | Glu | Asp | Gly | His | Thr | Leu | Phe | Asp | Tyr | Glu | Val | Arg | |
| | 50 | | | | | 55 | | | | | 60 | | | | | |
| ctg | aat | gac | acc | atc | cag | ctc | ctg | gtc | cgc | cag | agc | ctc | gtg | ctc | ccc | 240 |
| Leu | Asn | Asp | Thr | Ile | Gln | Leu | Leu | Val | Arg | Gln | Ser | Leu | Val | Leu | Pro | |
| 65 | | | | | 70 | | | | | 75 | | | | | 80 | |
| cac | agc | acc | aag | gag | cgg | gac | tcc | gag | ctc | tcc | gac | acc | gac | tcc | ggc | 288 |
| His | Ser | Thr | Lys | Glu | Arg | Asp | Ser | Glu | Leu | Ser | Asp | Thr | Asp | Ser | Gly | |
| | | | | 85 | | | | | 90 | | | | | 95 | | |
| tgc | tgc | ctg | ggc | cag | agt | gag | tca | gac | aag | tcc | tcc | acc | cac | ggt | gag | 336 |
| Cys | Cys | Leu | Gly | Gln | Ser | Glu | Ser | Asp | Lys | Ser | Ser | Thr | His | Gly | Glu | |
| | | | 100 | | | | | 105 | | | | | 110 | | | |
| gcg | gcc | gcc | gag | act | gac | agc | agg | cca | gcc | gat | gag | gac | atg | tgg | gat | 384 |
| Ala | Ala | Ala | Glu | Thr | Asp | Ser | Arg | Pro | Ala | Asp | Glu | Asp | Met | Trp | Asp | |
| | | 115 | | | | | 120 | | | | | 125 | | | | |
| gag | acg | gaa | ttg | ggg | ctg | tac | aag | gtc | aat | gag | tac | gtc | gat | gct | cgg | 432 |
| Glu | Thr | Glu | Leu | Gly | Leu | Tyr | Lys | Val | Asn | Glu | Tyr | Val | Asp | Ala | Arg | |
| | 130 | | | | | 135 | | | | | 140 | | | | | |
| gac | acg | aac | atg | ggg | gcg | tgg | ttt | gag | gcg | cag | gtg | gtc | agg | gtg | acg | 480 |
| Asp | Thr | Asn | Met | Gly | Ala | Trp | Phe | Glu | Ala | Gln | Val | Val | Arg | Val | Thr | |
| 145 | | | | | 150 | | | | | 155 | | | | | 160 | |
| cgg | aag | gcc | ccc | tcc | cgg | gac | gag | ccc | tgc | agc | tcc | acg | tcc | agg | ccg | 528 |
| Arg | Lys | Ala | Pro | Ser | Arg | Asp | Glu | Pro | Cys | Ser | Ser | Thr | Ser | Arg | Pro | |
| | | | | 165 | | | | | 170 | | | | | 175 | | |
| gcg | ctg | gag | gag | gac | gtc | att | tac | cac | gtg | aaa | tac | gac | gac | tac | ccg | 576 |
| Ala | Leu | Glu | Glu | Asp | Val | Ile | Tyr | His | Val | Lys | Tyr | Asp | Asp | Tyr | Pro | |
| | | | | 180 | | | | | 185 | | | | | 190 | | |
| gag | aac | ggc | gtg | gtc | cag | atg | aac | tcc | agg | gac | gtc | cga | gcg | cgc | gcc | 624 |
| Glu | Asn | Gly | Val | Val | Gln | Met | Asn | Ser | Arg | Asp | Val | Arg | Ala | Arg | Ala | |
| | | | 195 | | | | | 200 | | | | | 205 | | | |
| cgc | acc | atc | atc | aag | tgg | cag | gac | ctg | gag | gtg | ggc | cag | gtg | gtc | atg | 672 |
| Arg | Thr | Ile | Ile | Lys | Trp | Gln | Asp | Leu | Glu | Val | Gly | Gln | Val | Val | Met | |
| | | 210 | | | | | 215 | | | | | 220 | | | | |
| ctc | aac | tac | aac | ccc | gac | aac | ccc | aag | gag | cgg | ggc | ttc | tgg | tac | gac | 720 |
| Leu | Asn | Tyr | Asn | Pro | Asp | Asn | Pro | Lys | Glu | Arg | Gly | Phe | Trp | Tyr | Asp | |
| 225 | | | | | 230 | | | | | 235 | | | | | 240 | |
| gcg | gag | atc | tcc | agg | aag | cgc | gag | acc | agg | acg | gcg | cgg | gaa | ctc | tac | 768 |
| Ala | Glu | Ile | Ser | Arg | Lys | Arg | Glu | Thr | Arg | Thr | Ala | Arg | Glu | Leu | Tyr | |
| | | | | 245 | | | | | 250 | | | | | 255 | | |

-continued

| | | |
|---|---|---|
| gcc aac gtg gtg ctg ggg gat gat tct ctg aac gac tgt cgg atc atc<br>Ala Asn Val Val Leu Gly Asp Asp Ser Leu Asn Asp Cys Arg Ile Ile<br>260                                    265                        270 | 816 |
| ttc gtg gac gaa gtc ttc aag att gag cgg ccg ggt gaa ggg agc ccc<br>Phe Val Asp Glu Val Phe Lys Ile Glu Arg Pro Gly Glu Gly Ser Pro<br>275                                   280                         285 | 864 |
| atg gtt gac aac ccc atg aga cgg aag agc ggg ccg tcc tgc aag cac<br>Met Val Asp Asn Pro Met Arg Arg Lys Ser Gly Pro Ser Cys Lys His<br>290                                   295                        300 | 912 |
| tgc aag gac gac gtg aac aga ctc tgc agg gtc tgc gcc tgc cac ctg<br>Cys Lys Asp Asp Val Asn Arg Leu Cys Arg Val Cys Ala Cys His Leu<br>305                           310                        315                        320 | 960 |
| tgc ggg ggc cgg cag gac ccc gac aag cag ctc atg tgc gat gag tgc<br>Cys Gly Gly Arg Gln Asp Pro Asp Lys Gln Leu Met Cys Asp Glu Cys<br>                         325                             330                         335 | 1008 |
| gac atg gcc ttc cac atc tac tgc ctg gac ccg ccc ctc agc agt gtt<br>Asp Met Ala Phe His Ile Tyr Cys Leu Asp Pro Pro Leu Ser Ser Val<br>                    340                           345                        350 | 1056 |
| ccc agc gag gac gag tgg tac tgc cct gag tgc cgg aat gat gcc agc<br>Pro Ser Glu Asp Glu Trp Tyr Cys Pro Glu Cys Arg Asn Asp Ala Ser<br>                   355                          360                         365 | 1104 |
| gag gtg gta ctg gcg gga gag cgg ctg aga gag agc aag aag aat gcg<br>Glu Val Val Leu Ala Gly Glu Arg Leu Arg Glu Ser Lys Lys Asn Ala<br>370                                   375                        380 | 1152 |
| aag atg gcc tcg gcc aca tcg tcc tca cag cgg gac tgg ggc aag ggc<br>Lys Met Ala Ser Ala Thr Ser Ser Ser Gln Arg Asp Trp Gly Lys Gly<br>385                                   390                             395                        400 | 1200 |
| atg gcc tgt gtg ggc cgc acc aag gaa tgt acc atc gtc ccg tcc aac<br>Met Ala Cys Val Gly Arg Thr Lys Glu Cys Thr Ile Val Pro Ser Asn<br>                         405                             410                         415 | 1248 |
| cac tac gga ccc atc ccg ggg atc ccc gtg ggc acc atg tgg cgg ttc<br>His Tyr Gly Pro Ile Pro Gly Ile Pro Val Gly Thr Met Trp Arg Phe<br>                    420                           425                        430 | 1296 |
| cga gtc cag gtc agc gag tcg ggt gtc cat cgg ccc cac gtg gct ggc<br>Arg Val Gln Val Ser Glu Ser Gly Val His Arg Pro His Val Ala Gly<br>                         435                             440                         445 | 1344 |
| atc cat ggc cgg agc aac gac gga tcg tac tcc cta gtc ctg gcg ggg<br>Ile His Gly Arg Ser Asn Asp Gly Ser Tyr Ser Leu Val Leu Ala Gly<br>450                                   455                        460 | 1392 |
| ggc tat gag gat gat gtg gac cat ggg aat ttt ttc aca tac acg ggt<br>Gly Tyr Glu Asp Asp Val Asp His Gly Asn Phe Phe Thr Tyr Thr Gly<br>465                                   470                        475                        480 | 1440 |
| agt ggt ggt cga gat ctt tcc ggc aac aag agg acc gcg gaa cag tct<br>Ser Gly Gly Arg Asp Leu Ser Gly Asn Lys Arg Thr Ala Glu Gln Ser<br>                         485                             490                         495 | 1488 |
| tgt gat cag aaa ctc acc aac acc aac agg gcg ctg gct ctc aac tgc<br>Cys Asp Gln Lys Leu Thr Asn Thr Asn Arg Ala Leu Ala Leu Asn Cys<br>                         500                             505                         510 | 1536 |
| ttt gct ccc atc aat gac caa gaa ggg gcc gag gcc aag gac tgg cgg<br>Phe Ala Pro Ile Asn Asp Gln Glu Gly Ala Glu Ala Lys Asp Trp Arg<br>                    515                          520                         525 | 1584 |
| tcg ggg aag ccg gtc agg gtg gtg cgc aat gtc aag ggt ggc aag aat<br>Ser Gly Lys Pro Val Arg Val Val Arg Asn Val Lys Gly Gly Lys Asn<br>530                                   535                        540 | 1632 |
| agc aag tac gcc ccc gct gag ggc aac cgc tac gat ggc atc tac aag<br>Ser Lys Tyr Ala Pro Ala Glu Gly Asn Arg Tyr Asp Gly Ile Tyr Lys<br>545                                   550                        555                        560 | 1680 |
| gtt gtg aaa tac tgg ccc gag aag ggg aag tcc ggg ttt ctc gtg tgg<br>Val Val Lys Tyr Trp Pro Glu Lys Gly Lys Ser Gly Phe Leu Val Trp<br>                         565                             570                         575 | 1728 |

-continued

```
cgc tac ctt ctg cgg agg gac gat gat gag cct ggc cct tgg acg aag      1776
Arg Tyr Leu Leu Arg Arg Asp Asp Asp Glu Pro Gly Pro Trp Thr Lys
            580                 585                 590 gag ggg aag gac cgg atc aag aag ctg ggg ctg acc atg cag tat cca      1824
Glu Gly Lys Asp Arg Ile Lys Lys Leu Gly Leu Thr Met Gln Tyr Pro
        595                 600                 605 gaa ggc tac ctg gaa gcc ctg gcc aac cga gag cga gag aag gag aac      1872
Glu Gly Tyr Leu Glu Ala Leu Ala Asn Arg Glu Arg Glu Lys Glu Asn
    610                 615                 620 agc aag agg gag gag gag gag cag cag gag ggg ggc ttc gcg tcc ccc      1920
Ser Lys Arg Glu Glu Glu Glu Gln Gln Glu Gly Gly Phe Ala Ser Pro
625                 630                 635                 640 agg acg ggc aag ggc aag tgg aag cgg aag tcg gca gga ggt ggc ccg      1968
Arg Thr Gly Lys Gly Lys Trp Lys Arg Lys Ser Ala Gly Gly Gly Pro
                645                 650                 655 agc agg gcc ggg tcc ccg cgc cgg aca tcc aag aaa acc aag gtg gag      2016
Ser Arg Ala Gly Ser Pro Arg Arg Thr Ser Lys Lys Thr Lys Val Glu
            660                 665                 670 ccc tac agt ctc acg gcc cag cag agc agc ctc atc aga gag gac aag      2064
Pro Tyr Ser Leu Thr Ala Gln Gln Ser Ser Leu Ile Arg Glu Asp Lys
        675                 680                 685 agc aac gcc aag ctg tgg aat gag gtc ctg gcg tca ctc aag gac cgg      2112
Ser Asn Ala Lys Leu Trp Asn Glu Val Leu Ala Ser Leu Lys Asp Arg
    690                 695                 700 ccg gcg agc ggc agc ccg ttc cag ttg ttc ctg agt aaa gtg gag gag      2160
Pro Ala Ser Gly Ser Pro Phe Gln Leu Phe Leu Ser Lys Val Glu Glu
705                 710                 715                 720 acg ttc cag tgt atc tgc tgt cag gag ctg gtg ttc cgg ccc atc acg      2208
Thr Phe Gln Cys Ile Cys Cys Gln Glu Leu Val Phe Arg Pro Ile Thr
                725                 730                 735 acc gtg tgc cag cac aac gtg tgc aag gac tgc ctg gac aga tcc ttt      2256
Thr Val Cys Gln His Asn Val Cys Lys Asp Cys Leu Asp Arg Ser Phe
            740                 745                 750 cgg gca cag gtg ttc agc tgc cct gcc tgc cgc tac gac ctg ggc cgc      2304
Arg Ala Gln Val Phe Ser Cys Pro Ala Cys Arg Tyr Asp Leu Gly Arg
        755                 760                 765 agc tat gcc atg cag gtg aac cag cct ctg cag acc gtc ctc aac cag      2352
Ser Tyr Ala Met Gln Val Asn Gln Pro Leu Gln Thr Val Leu Asn Gln
    770                 775                 780 ctc ttc ccc ggc tac ggc aat ggc cgg tga                              2382
Leu Phe Pro Gly Tyr Gly Asn Gly Arg
785                 790
```

<210> SEQ ID NO 2
<211> LENGTH: 793
<212> TYPE: PRT
<213> ORGANISM: Homo sapiens

<400> SEQUENCE: 2

```
Met Trp Ile Gln Val Arg Thr Met Asp Gly Arg Gln Thr His Thr Val
  1               5                  10                  15

Asp Ser Leu Ser Arg Leu Thr Lys Val Glu Glu Leu Arg Arg Lys Ile
             20                  25                  30

Gln Glu Leu Phe His Val Glu Pro Gly Leu Gln Arg Leu Phe Tyr Arg
         35                  40                  45

Gly Lys Gln Met Glu Asp Gly His Thr Leu Phe Asp Tyr Glu Val Arg
     50                  55                  60

Leu Asn Asp Thr Ile Gln Leu Leu Val Arg Gln Ser Leu Val Leu Pro
 65                  70                  75                  80
```

-continued

```
His Ser Thr Lys Glu Arg Asp Ser Glu Leu Ser Asp Thr Asp Ser Gly
                85                  90                  95

Cys Cys Leu Gly Gln Ser Glu Ser Asp Lys Ser Ser Thr His Gly Glu
            100                 105                 110

Ala Ala Ala Glu Thr Asp Ser Arg Pro Ala Asp Glu Asp Met Trp Asp
        115                 120                 125

Glu Thr Glu Leu Gly Leu Tyr Lys Val Asn Glu Tyr Val Asp Ala Arg
    130                 135                 140

Asp Thr Asn Met Gly Ala Trp Phe Glu Ala Gln Val Val Arg Val Thr
145                 150                 155                 160

Arg Lys Ala Pro Ser Arg Asp Glu Pro Cys Ser Ser Thr Ser Arg Pro
                165                 170                 175

Ala Leu Glu Glu Asp Val Ile Tyr His Val Lys Tyr Asp Asp Tyr Pro
            180                 185                 190

Glu Asn Gly Val Val Gln Met Asn Ser Arg Asp Val Arg Ala Arg Ala
        195                 200                 205

Arg Thr Ile Ile Lys Trp Gln Asp Leu Glu Val Gly Gln Val Val Met
    210                 215                 220

Leu Asn Tyr Asn Pro Asp Asn Pro Lys Glu Arg Gly Phe Trp Tyr Asp
225                 230                 235                 240

Ala Glu Ile Ser Arg Lys Arg Glu Thr Arg Thr Ala Arg Glu Leu Tyr
                245                 250                 255

Ala Asn Val Val Leu Gly Asp Asp Ser Leu Asn Asp Cys Arg Ile Ile
            260                 265                 270

Phe Val Asp Glu Val Phe Lys Ile Glu Arg Pro Gly Glu Gly Ser Pro
        275                 280                 285

Met Val Asp Asn Pro Met Arg Arg Lys Ser Gly Pro Ser Cys Lys His
    290                 295                 300

Cys Lys Asp Asp Val Asn Arg Leu Cys Arg Val Cys Ala Cys His Leu
305                 310                 315                 320

Cys Gly Gly Arg Gln Asp Pro Asp Lys Gln Leu Met Cys Asp Glu Cys
                325                 330                 335

Asp Met Ala Phe His Ile Tyr Cys Leu Asp Pro Pro Leu Ser Ser Val
            340                 345                 350

Pro Ser Glu Asp Glu Trp Tyr Cys Pro Glu Cys Arg Asn Asp Ala Ser
        355                 360                 365

Glu Val Val Leu Ala Gly Glu Arg Leu Arg Glu Ser Lys Lys Asn Ala
    370                 375                 380

Lys Met Ala Ser Ala Thr Ser Ser Gln Arg Asp Trp Gly Lys Gly
385                 390                 395                 400

Met Ala Cys Val Gly Arg Thr Lys Glu Cys Thr Ile Val Pro Ser Asn
                405                 410                 415

His Tyr Gly Pro Ile Pro Gly Ile Pro Val Gly Thr Met Trp Arg Phe
            420                 425                 430

Arg Val Gln Val Ser Glu Ser Gly Val His Arg Pro His Val Ala Gly
        435                 440                 445

Ile His Gly Arg Ser Asn Asp Gly Ser Tyr Ser Leu Val Leu Ala Gly
    450                 455                 460

Gly Tyr Glu Asp Asp Val Asp His Gly Asn Phe Phe Thr Tyr Thr Gly
465                 470                 475                 480

Ser Gly Gly Arg Asp Leu Ser Gly Asn Lys Arg Thr Ala Glu Gln Ser
                485                 490                 495
```

-continued

```
Cys Asp Gln Lys Leu Thr Asn Thr Asn Arg Ala Leu Ala Leu Asn Cys
        500                 505                 510

Phe Ala Pro Ile Asn Asp Gln Glu Gly Ala Glu Ala Lys Asp Trp Arg
        515                 520                 525

Ser Gly Lys Pro Val Arg Val Arg Asn Val Lys Gly Gly Lys Asn
        530                 535                 540

Ser Lys Tyr Ala Pro Ala Glu Gly Asn Arg Tyr Asp Gly Ile Tyr Lys
545                 550                 555                 560

Val Val Lys Tyr Trp Pro Glu Lys Gly Lys Ser Gly Phe Leu Val Trp
                565                 570                 575

Arg Tyr Leu Leu Arg Arg Asp Asp Glu Pro Gly Pro Trp Thr Lys
                580                 585                 590

Glu Gly Lys Asp Arg Ile Lys Lys Leu Gly Leu Thr Met Gln Tyr Pro
                595                 600                 605

Glu Gly Tyr Leu Glu Ala Leu Ala Asn Arg Glu Arg Glu Lys Glu Asn
        610                 615                 620

Ser Lys Arg Glu Glu Glu Gln Glu Gly Gly Phe Ala Ser Pro
625                 630                 635                 640

Arg Thr Gly Lys Gly Lys Trp Lys Arg Ser Ala Gly Gly Pro
                645                 650                 655

Ser Arg Ala Gly Ser Pro Arg Arg Thr Ser Lys Lys Thr Lys Val Glu
        660                 665                 670

Pro Tyr Ser Leu Thr Ala Gln Gln Ser Ser Leu Ile Arg Glu Asp Lys
        675                 680                 685

Ser Asn Ala Lys Leu Trp Asn Glu Val Leu Ala Ser Leu Lys Asp Arg
        690                 695                 700

Pro Ala Ser Gly Ser Pro Phe Gln Leu Phe Leu Ser Lys Val Glu Glu
705                 710                 715                 720

Thr Phe Gln Cys Ile Cys Cys Gln Glu Leu Val Phe Arg Pro Ile Thr
                725                 730                 735

Thr Val Cys Gln His Asn Val Cys Lys Asp Cys Leu Asp Arg Ser Phe
                740                 745                 750

Arg Ala Gln Val Phe Ser Cys Pro Ala Cys Arg Tyr Asp Leu Gly Arg
        755                 760                 765

Ser Tyr Ala Met Gln Val Asn Gln Pro Leu Gln Thr Val Leu Asn Gln
770                 775                 780

Leu Phe Pro Gly Tyr Gly Asn Gly Arg
785                 790

<210> SEQ ID NO 3
<211> LENGTH: 45
<212> TYPE: DNA
<213> ORGANISM: Homo sapiens
<220> FEATURE:
<221> NAME/KEY: CDS
<222> LOCATION: (1)..(45)

<400> SEQUENCE: 3 acc cac ggt gag gcg gcc gcc gag act gac agc agg cca gcc gat    45
Thr His Gly Glu Ala Ala Ala Glu Thr Asp Ser Arg Pro Ala Asp
  1               5                   10                  15

<210> SEQ ID NO 4
<211> LENGTH: 15
<212> TYPE: PRT
<213> ORGANISM: Homo sapiens

<400> SEQUENCE: 4
```

-continued

```
Thr His Gly Glu Ala Ala Ala Glu Thr Asp Ser Arg Pro Ala Asp
  1               5                  10                  15

<210> SEQ ID NO 5
<211> LENGTH: 78
<212> TYPE: DNA
<213> ORGANISM: Homo sapiens
<220> FEATURE:
<221> NAME/KEY: CDS
<222> LOCATION: (1)..(78)

<400> SEQUENCE: 5 atg gtt gac aac ccc atg aga cgg aag agc ggg ccg tcc tgc aag cac      48
Met Val Asp Asn Pro Met Arg Arg Lys Ser Gly Pro Ser Cys Lys His
  1               5                  10                  15 tgc aag gac gac gtg aac aga ctc tgc agc                              78
Cys Lys Asp Asp Val Asn Arg Leu Cys Ser
             20                  25

<210> SEQ ID NO 6
<211> LENGTH: 26
<212> TYPE: PRT
<213> ORGANISM: Homo sapiens

<400> SEQUENCE: 6

Met Val Asp Asn Pro Met Arg Arg Lys Ser Gly Pro Ser Cys Lys His
  1               5                  10                  15

Cys Lys Asp Asp Val Asn Arg Leu Cys Ser
             20                  25

<210> SEQ ID NO 7
<211> LENGTH: 525
<212> TYPE: DNA
<213> ORGANISM: Homo sapiens
<220> FEATURE:
<221> NAME/KEY: CDS
<222> LOCATION: (1)..(522)

<400> SEQUENCE: 7 cga gag aag gag aac agc aag agg gag gag gag gag cag cag gag ggg      48
Arg Glu Lys Glu Asn Ser Lys Arg Glu Glu Glu Glu Gln Gln Glu Gly
  1               5                  10                  15 ggc ttc gcg tcc ccc agg acg ggc aag ggc aag tgg aag cgg aag tcg      96
Gly Phe Ala Ser Pro Arg Thr Gly Lys Gly Lys Trp Lys Arg Lys Ser
             20                  25                  30 gca gga ggt ggc ccg agc agg gcc ggg tcc ccg cgc cgg aca tcc aag     144
Ala Gly Gly Gly Pro Ser Arg Ala Gly Ser Pro Arg Arg Thr Ser Lys
         35                  40                  45 aaa acc aag gtg gag ccc tac agt ctc acg gcc cag cag agc agc ctc     192
Lys Thr Lys Val Glu Pro Tyr Ser Leu Thr Ala Gln Gln Ser Ser Leu
     50                  55                  60 atc aga gag gac aag agc aac gcc aag ctg tgg aat gag gtc ctg gcg     240
Ile Arg Glu Asp Lys Ser Asn Ala Lys Leu Trp Asn Glu Val Leu Ala
 65                  70                  75                  80 tca ctc aag gac cgg ccg gcg agc ggc agc ccg ttc cag ttg ttc ctg     288
Ser Leu Lys Asp Arg Pro Ala Ser Gly Ser Pro Phe Gln Leu Phe Leu
                 85                  90                  95 agt aaa gtg gag gag acg ttc cag tgt atc tgc tgt cag gag ctg gtg     336
Ser Lys Val Glu Glu Thr Phe Gln Cys Ile Cys Cys Gln Glu Leu Val
            100                 105                 110 ttc cgg ccc atc acg acc gtg tgc cag cac aac gtg tgc aag gac tgc     384
Phe Arg Pro Ile Thr Thr Val Cys Gln His Asn Val Cys Lys Asp Cys
        115                 120                 125
```

| ctg gac aga tcc ttt cgg gca cag gtg ttc agc tgc cct gcc tgc cgc | 432 |
|---|---|
| Leu Asp Arg Ser Phe Arg Ala Gln Val Phe Ser Cys Pro Ala Cys Arg | |
| 130 135 140 | |

| tac gac ctg ggc cgc agc tat gcc atg cag gtg aac cag cct ctg cag | 480 |
|---|---|
| Tyr Asp Leu Gly Arg Ser Tyr Ala Met Gln Val Asn Gln Pro Leu Gln | |
| 145 150 155 160 | |

| acc gtc ctc aac cag ctc ttc ccc ggc tac ggc aat ggc cgg tga | 525 |
|---|---|
| Thr Val Leu Asn Gln Leu Phe Pro Gly Tyr Gly Asn Gly Arg | |
| 165 170 | |

<210> SEQ ID NO 8
<211> LENGTH: 174
<212> TYPE: PRT
<213> ORGANISM: Homo sapiens

<400> SEQUENCE: 8

Arg Glu Lys Glu Asn Ser Lys Arg Glu Glu Glu Gln Gln Glu Gly
1               5                   10                  15

Gly Phe Ala Ser Pro Arg Thr Gly Lys Gly Lys Trp Lys Arg Lys Ser
            20                  25                  30

Ala Gly Gly Gly Pro Ser Arg Ala Gly Ser Pro Arg Arg Thr Ser Lys
        35                  40                  45

Lys Thr Lys Val Glu Pro Tyr Ser Leu Thr Ala Gln Gln Ser Ser Leu
    50                  55                  60

Ile Arg Glu Asp Lys Ser Asn Ala Lys Leu Trp Asn Glu Val Leu Ala
65                  70                  75                  80

Ser Leu Lys Asp Arg Pro Ala Ser Gly Ser Pro Phe Gln Leu Phe Leu
                85                  90                  95

Ser Lys Val Glu Glu Thr Phe Gln Cys Ile Cys Cys Gln Glu Leu Val
            100                 105                 110

Phe Arg Pro Ile Thr Thr Val Cys Gln His Asn Val Cys Lys Asp Cys
        115                 120                 125

Leu Asp Arg Ser Phe Arg Ala Gln Val Phe Ser Cys Pro Ala Cys Arg
    130                 135                 140

Tyr Asp Leu Gly Arg Ser Tyr Ala Met Gln Val Asn Gln Pro Leu Gln
145                 150                 155                 160

Thr Val Leu Asn Gln Leu Phe Pro Gly Tyr Gly Asn Gly Arg
                165                 170

<210> SEQ ID NO 9
<211> LENGTH: 324
<212> TYPE: DNA
<213> ORGANISM: Homo sapiens

<400> SEQUENCE: 9
atgtggatcc aggttcggac catggatggg aggcagaccc acacggtgga ctcgctgtcc      60
aggctgacca aggtggagga gctgaggcgg aagatccagg agctgttcca cgtggagcca     120
ggcctgcaga ggctgttcta caggggcaaa cagatggagg acggccatac cctcttcgac     180
tacgaggtcc gcctgaatga caccatccag ctcctggtcc gccagagcct cgtgctcccc     240
cacagcacca aggagcggga ctccgagctc tccgacaccg actccggctg ctgcctgggc     300
cagagtgagt cagacaagtc ctcc                                            324

<210> SEQ ID NO 10
<211> LENGTH: 495
<212> TYPE: DNA
<213> ORGANISM: Homo sapiens

```
<400> SEQUENCE: 10
gaggacatgt gggatgagac ggaattgggg ctgtacaagg tcaatgagta cgtcgatgct      60
cgggacacga acatgggggc gtggtttgag gcgcaggtgg tcagggtgac gcggaaggcc     120
ccctcccggg acgagccctg cagctccacg tccaggccgg cgctggagga ggacgtcatt     180
taccacgtga atacgacga ctacccggag aacggcgtgg tccagatgaa ctccagggac     240
gtccgagcgc gcgcccgcac catcatcaag tggcaggacc tggaggtggg ccaggtggtc     300
atgctcaact acaaccccga caaccccaag gagcggggct tctggtacga cgcggagatc     360
tccaggaagc gcgagaccag gacggcgcgg gaactctacg ccaacgtggt gctgggggat     420
gattctctga cgactgtcg gatcatcttc gtggacgaag tcttcaagat tgagcggccg     480
ggtgaaggga gcccc                                                      495

<210> SEQ ID NO 11
<211> LENGTH: 915
<212> TYPE: DNA
<213> ORGANISM: Homo sapiens

<400> SEQUENCE: 11
gtctgcgcct gccacctgtg cgggggccgg caggacccg acaagcagct catgtgcgat      60
gagtgcgaca tggccttcca catctactgc ctggacccgc ccctcagcag tgttcccagc     120
gaggacgagt ggtactgccc tgagtgccgg aatgatgcca gcgaggtggt actggcggga     180
gagcggctga gagagagcaa gaagaatgcg aagatggcct cggccacatc gtcctcacag     240
cgggactggg gcaagggcat ggcctgtgtg ggccgcacca aggaatgtac catcgtcccg     300
tccaaccact acgacccat cccggggatc ccgtgggca ccatgtggcg gttccgagtc     360
caggtcagcg agtcgggtgt ccatcggccc cacgtggctg gcatccatgg ccggagcaac     420
gacggatcgt actccctagt cctggcgggg ggctatgagg atgatgtgga ccatgggaat     480
tttttcacat acacgggtag tggtggtcga gatctttccg gcaacaagag gaccgcggaa     540
cagtcttgtg atcagaaact caccaacacc aacaggcgc tggctctcaa ctgctttgct     600
cccatcaatg accaagaagg ggccgaggcc aaggactggc ggtcggggaa gccggtcagg     660
gtggtgcgca atgtcaaggg tggcaagaat agcaagtacg cccccgctga gggcaaccgc     720
tacgatggca tctacaaggt tgtgaaatac tggcccgaga aggggaagtc cgggtttctc     780
gtgtggcgct accttctgcg gagggacgat gatgagcctg gcccttggac gaaggagggg     840
aaggaccgga tcaagaagct ggggctgacc atgcagtatc cagaaggcta cctggaagcc     900
ctggccaacc gagag                                                      915

<210> SEQ ID NO 12
<211> LENGTH: 1369
<212> TYPE: DNA
<213> ORGANISM: Homo sapiens

<400> SEQUENCE: 12
ggcagcgttt gccgagcggg cgctccgggt cgcacgcaag tccgcgcggg gtccgggcca      60
cgcacgcggt ttcatcgcca tccccagccg ggccaggcgc gcaggcagac aagctgttcg     120
cggcgaccgg agaggtgagc gggcgggccg ggtcgggtg ccagcccggg ccgggcgcac     180
ggggctcggg aactttgcaa aactttcccg cgcggccagc ccgggcgcac gcatgtcccg     240
cactctgtcc cgggatccag ggcctcccct tccacctaac cctcgggaat cgttccccgg     300
```

```
cacacatccg gctggagccg ggaccagcgc tgcgtccccg gagcccggcg ggggtcgag     360 cgcgccgggt gggggagggc ctggcgagcc gccggggagg atgtcaggct ccgcgcctgc     420
gcgcggggcg ccccgcgatt caattgtcgc gcccgagccc gatttcgcgc gccctgagtt     480
ccccgggagc atctgggcca atggggagcg agcggggcg gcggccggg tgctgcggag       540 ccaataagag gcggctcaag tgaaggggg cgggacttga cgagcggggg cccctctgt       600 agtcccggcg gcggggtgg gcgtgggctc gctggcgcga cccgcgcggg ccagtgggag      660
tgcgggaggg acgccgaggg tccagggttt ggaggggcgc gagctgccgg gggttggagg    720
tcgaggtgag tcgcggggcg cgcgcgctcg cgggtggccg ggacggggcg cggttaccat     780
ggccaccgcg gggcgggccc ggtcgcgcac gcgcgcgggg ggggccggca aggaggggg     840 gcgtgggcac cgagggtcc cggggtccgc ggatctcggg tggggttttt cccatttcag       900
tggcacttgg ttaagttccc ccgggacctt ctgaagttcc ggcccgcgct ggactttctg     960
ggattccctc ttccgtaaat aggaatccga ggaatgaatg aatcaatgaa tgaatgaata    1020
aacgaaccaa ctcgggccac ttggcccggg cctcctttct cctctggtcg tggggaagga    1080
gggatgggtt ggaccttctg ctttttctttc aattccctct tttcattctc cttcctcctc    1140
aatcttcaac acttggctag tcgttaatgc cttaagtgct taatttgttg tgtctggtcc    1200
tggccagggt ctggctgtac aggaggactg gaagggcatc ctgggagttt cctggtgtcc    1260
acaggccgga caaaagcaac cccgactcct tagagcatgg catggctcag aggtgctggt    1320
aaaactgatg ggggtttatg ctgtccctcc cctcagcgcc gacaccatg              1369
```

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aattcgattg gttctgattg gttctgattg gttctt                             36

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ctagaagaac caatcagaac caatcagaac caatcg                             36

<210> SEQ ID NO 15
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aattcggggc ggggccgggg cgggcccggg gcggggct                           38

<210> SEQ ID NO 16
<211> LENGTH: 39
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 16
ctagagcccc gccccggccc cgccccggcc ccgccccgg                              39

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
agtcagggat tggctggtct g                                                 21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cagaccagcc aatccctgac t                                                 21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
aagctacgat tggttcttct g                                                 21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cagaagaacc aatcgtagct t                                                 21

<210> SEQ ID NO 21
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ataaaggcaa gctacgattg gttcttctgg acggagac                               38

<210> SEQ ID NO 22
<211> LENGTH: 39
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 22
gtctccgtcc agaagaacca atcgtagctt gccttttat                              39

<210> SEQ ID NO 23
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gaattcgagg gtaaaggggc ggggttgagg cagatgcca                              39

<210> SEQ ID NO 24
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tggcatctgc ctcaaccccg cccttaccc tcgaattc                                38
```